United States Patent [19]

McCall et al.

[11] 4,166,062
[45] Aug. 28, 1979

[54] 1-ALKOXYETHANOL-ISOCHROMANS, -ISOTHIOCHROMANS, -2-BENZOXEPINS, AND -2-BENZOTHIEPINS

[75] Inventors: John M. McCall; Ruth E. TenBrink, both of Kalamazoo, Mich.

[73] Assignee: The Upjohn Company, Kalamazoo, Mich.

[21] Appl. No.: 927,152

[22] Filed: Jul. 21, 1978

[51] Int. Cl.$^2$ .............. C07D 313/08; C07D 337/08; C07D 311/02; C07D 323/00
[52] U.S. Cl. ............................ 260/333; 549/9; 549/12; 260/345.2; 260/338; 549/23; 549/26; 549/27; 544/145; 544/151; 544/376; 544/378; 544/147; 544/148; 544/150; 544/370; 546/197; 546/202; 546/196; 546/199; 546/148

[58] Field of Search ............ 260/333, 327 B, 327 TH, 260/345.2, 338

[56] References Cited
U.S. PATENT DOCUMENTS
3,859,306  1/1975  Freedman ........................ 260/333

Primary Examiner—John M. Ford
Assistant Examiner—Robert C. Whittenbaugh
Attorney, Agent, or Firm—Sidney B. Williams, Jr,

[57] ABSTRACT

1-Alkoxyethanol-isochromas, -isothiochromas, -2-benzoxepins, and -2-benzothiepins are described. These compounds are useful for preparing the corresponding aminoalkoxyalkyl derivatives that possess antihypertensive and CNS activity.

4 Claims, No Drawings

1-ALKOXYETHANOL-ISOCHROMANS, -ISOTHIOCHROMANS, -2-BENZOXEPINS, AND -2-BENZOTHIEPINS

CROSS REFERENCE TO RELATED APPLICATION

The compounds of this invention are useful for preparing some of the aminoalkoxyalkyl derivatives described and/or claimed in U.S. application Ser. No. 847,350, filed Oct. 31, 1977, and U.S. application Ser. No. 847,371, filed Oct. 31, 1977. They are also useful for preparing the isochromans, isothiochromans, 2-benzoxepins and 2-benzothiepins described and claimed in U.S. application Ser. No. 858,303, filed Dec. 7, 1977.

BACKGROUND OF THE INVENTION

1. Field of the Invention

This invention relates to novel 1-alkoxyethanol-isochromans, -isothiochromans, -2-benzoxepins and -2-benzothiepins and methods for preparing them.

2. The Prior Art

1-Substituted isochromans are known for a variety of uses. For example, U.S. Pat. No. 3,467,675, Sept. 16, 1969 (Petersen), teaches 1-alkyl- or 1-aryl-1-aminoalkyl-isochromans which are disclosed to treat physiological-psychological abnormalities. Specifically, Petersen teaches the use of the compounds for treatment of endogenic depression. Japanese Pat. No. J5 1125-287, Nov. 1, 1976 (Takeda) (Derwent 94938X) and Netherlands Pat. No. 7605-36, July 5, 1977 (Takeda) (Derwent 50610Y) also teach 1-aminoalkyl isochromans. The Takeda compounds are disclosed to be useful as anti-depression agents, analgesics, diuretics, anti-inflammatory agents, hypotensives and for the treatment of bronchial asthma.

SUMMARY OF THE INVENTION

The invention comprises compounds of the formula:

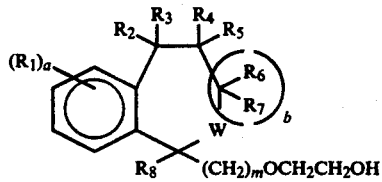

wherein
$R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;
a is one through three;
b is zero or one;
$R_2$ through $R_7$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, or $R_6$ and $R_7$ are taken together with the carbon to which they are attached; cycloalkyl of four through seven carbons when $R_2$ and $R_4$ or $R_4$ and $R_6$ are taken together with the carbons to which they are attached; and cycloalkyl of five or six carbons, with the proviso that no more than one ring may be attached to any one carbon and that at least two of $R_2$ through $R_7$ are hydrogen.
$R_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;
m is one to three; and
W is oxygen or sulfur.

DETAILED DESCRIPTION OF THE INVENTION

Compounds of formula I wherein b is 1 are prepared in accordance with the following flow chart:

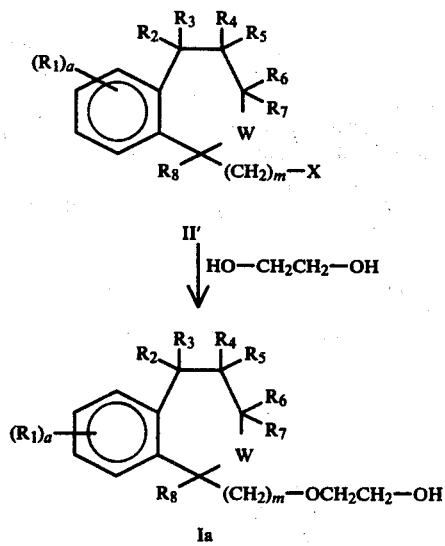

wherein a, m, W and $R_1$ through $R_8$ are the same as defined above, and X is a halogen group.

This reaction is conducted in the presence of an acid acceptor such as di-isopropylethylamine, at a temperature of between 20° C. and 100° C. for a period of about 20 to 120 hours. Other suitable acid acceptors include other trialkylamines e.g., triethylamine, DBU, inorganic salts, e.g. barium carbonate.

The products of Formula I can be obtained from the reaction mixture utilizing standard methods, for example, extraction, chromatography, crystallization and combinations thereof.

The compounds of formula I wherein b is zero, m is 1, and $R_1$ through $R_5$, $R_8$, a, and W are as defined above, are advantageously prepared by the route described in the following chart:

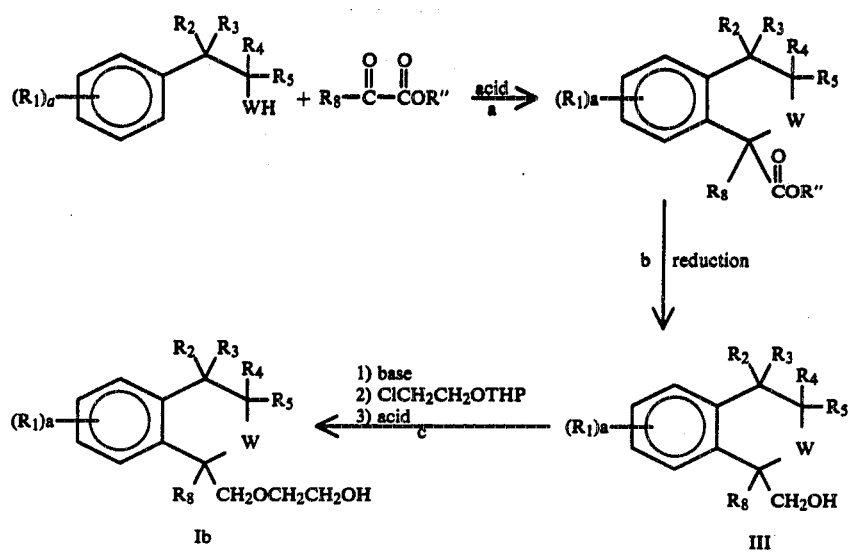

wherein R″ is alkyl of one through three carbon atoms, inclusive.

Step a is advantageously carried out in the presence of acids, e.g. BF$_3$.Et$_2$O, trifluoroacetic acid, p-toluenesulfonic acid, in solvents such as nitromethane or methylene chloride, at 0° to about 30° C.

Step b is carried out by use of conventional reducing agents, e.g. lithium aluminum hydride in non-polar solvents such as tetrahydrofuran at 0° to 30° C.

Step c is advantageously performed by reaction of an easily cleavable ether (e.g. tetrahydropyranyl ether) of the desired 2-haloethanol on the alkoxide of compound II′ at 20°–100° C. in a compatible non-polar solvent followed by cleavage of the ether under acidic conditions to give the compounds of formula Ib.

The compounds of Formula II used in the preparation of compounds of formula I can be prepared according to the following schematic flow chart:

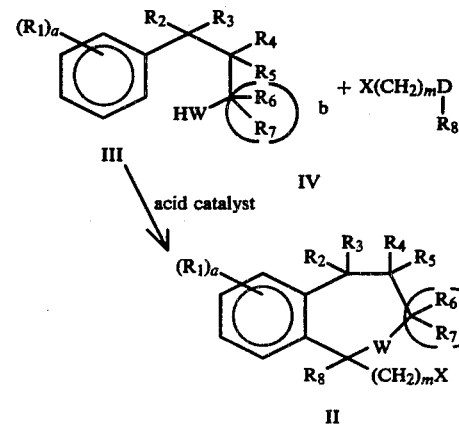

X is halo,
D is

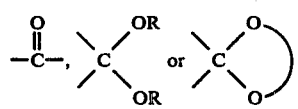

where R is alkyl of one through two carbons, i.e. ketal or acetal functionality, and all the other terms are as defined above.

The reaction can be performed in the absence of solvent but a solvent such as methylene chloride, nitromethane tetrahydrofuran (THF), ethylether, carbon disulfide, benzene, or toluene is preferred. Preferred temperature is about 25° but temperatures from 0° to 60° are acceptable.

The compounds (II) obtained can be recovered and purified by conventional methods, for example, extraction, chromatography and crystallization.

The alcohols of structure III (W=O), or Va, are readily available or can be prepared by methods well known in the art. See, for example, C. D. Gutsche, "The Chemistry of Carbonyl Compounds", Prentice-Hall, N.J., 1967; Organic Syntheses, Coll. Vol. II, John Wiley, p. 408.

The thiols of structure III (W=S) can be prepared from the alcohols via their bromides in accordance with the following flow chart, or by other literature methods for example, see Frank and Smith, J. Amer. Chem. Soc., 68, 2103 (1946).

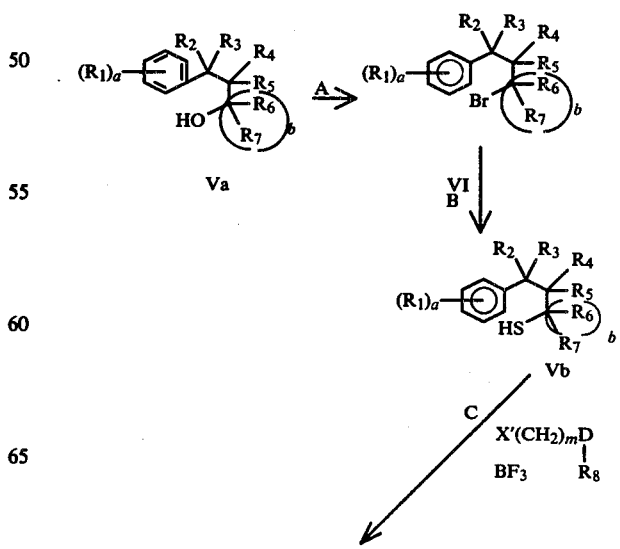

alcohol starting materials (Va) can be followed as examples:

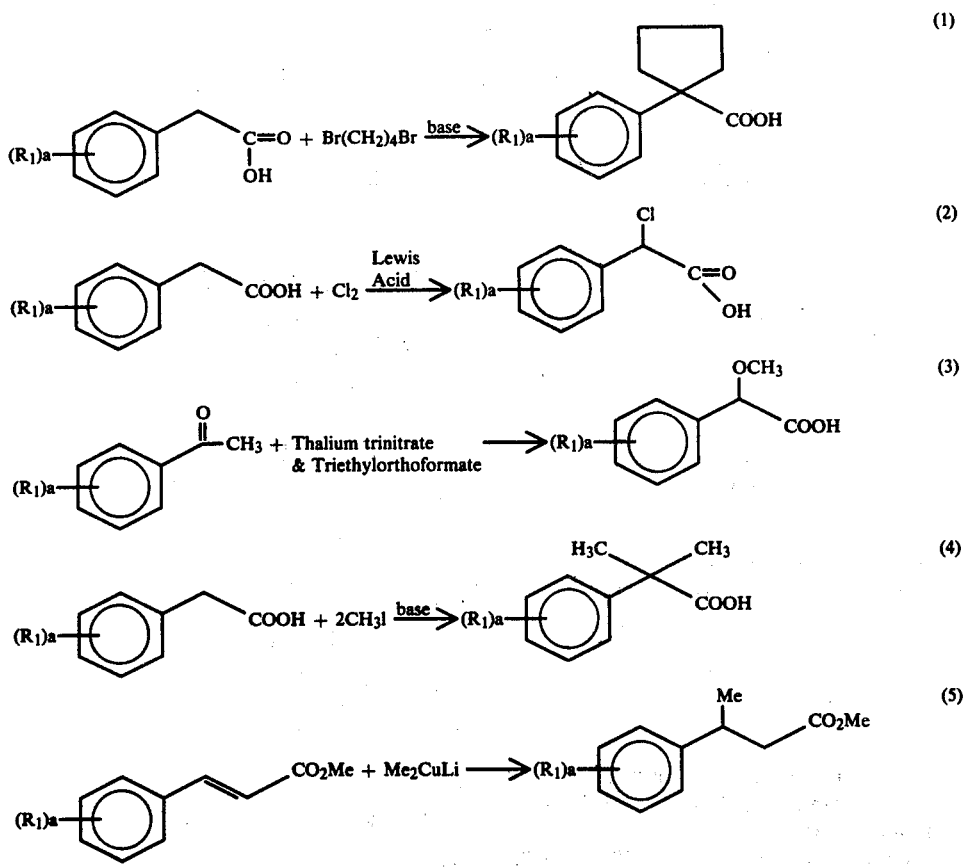

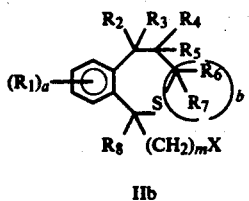

IIb wherein m is 1 to 3 and a, b, $R_1$ through $R_8$ and D are as above, and X is chloro or bromo.

In step A, the alcohol of formula Va can be converted to the bromide of formula VI by various procedures known to those skilled in the art. For example, it may be reacted with phosphorus tribromide or hydrogen bromide as is described in J. March, "Advanced Organic Chemistry", McGraw-Hill, 1968, p. 343.

In step B the bromide of formula VI is reacted with a mercaptide, for example sodium mercaptide, to give the thiol of formula Vb.

In step C the thiol of formula Vb is reacted with the appropriate acetal, ketal, ketone, or aldehyde in the presence of an acid catalyst, e.g. $BF_3$, to give the halide of formula IIb.

For the preparation of compounds of formula I wherein at least one of $R_2$ through $R_7$ is other than hydrogen, and are alkyl, halo, alkoxy, cycloalkyl, and b=0,1, the following known types of reactions (1-5) for the preparation of the ester or acid precursors to the Each acid or ester can then be reduced by conventional procedures (e.g. with lithium aluminum hydride in THF or sodium borohydride-Ethanol) to the alcohol and subsequently treated with compounds IV, to give the precursor 1-(haloalkyl)-1-$R_8$ isochromans or benzoxepins which can then be reacted as described above with ethylene glycol to give the corresponding formula I compounds. When it is desired that W=S, the thiols corresponding to these substituted alcohols be prepared and the methods shown in the flow scheme for preparing compounds of formula IIb can be used.

The above reactions for placing substituents on the carbon alpha to the acid function in a chain are known in the art and are only given as representative. They are not to be construed as limiting.

Reaction type (1) has been described in Organic Syntheses (Wiley) collective volumes I-IV, and in J. March, Advanced Organic Chemistry, McGraw-Hill, (1968) p. 360. Reaction type (2) is also in Organic Syntheses and in J. March, p. 460 (it is known as the Hell-Volhard-Zelinskii reaction).

Reaction type (3) has been described in J. Amer. Chem. Soc., 98, 6750 (1976).

Reaction type (4) is known in the art for alkylation at acidic hydrogen sites - this type of reaction can be found in Organic Syntheses (Wiley), Volume 50, p. 58 (1970).

Reaction type (5) can be carried out according to Katzenellenbogen, J. Org. Chem. 38, 2733 (1973).

The following is a preparation which can also be used for the 2-benzoxepines of formula I where m=2.

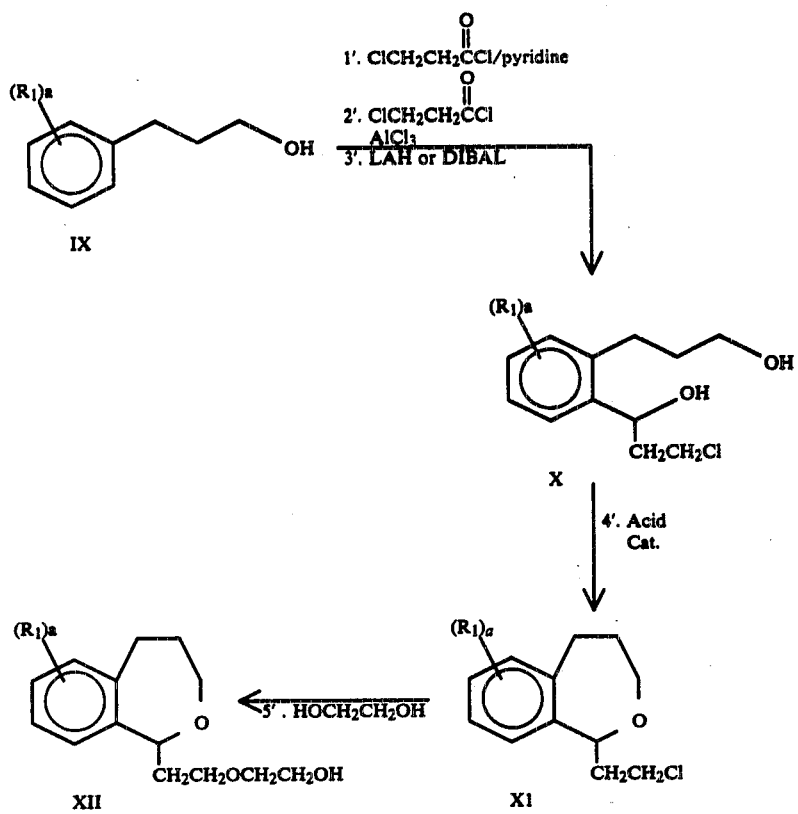

Step 1' is carried out in the presence of an acid scavenger, for example, pyridine, and is a conventional acylation reaction.

Step 2' is performed in an aromatic solvent such as toluene, in nitromethane or in a halocarbon such as methylene chloride. Other catalysts such as $SnCl_4$ or $FeCl_3$ are usable but $AlCl_3$ is preferred. Temperature can range from 10° to 100°.

Step 3' may be conducted in non-polar solvents such as tetrahydrofuran (THF), ether, or toluene.

The acid catalysts for step 4' include mineral acids and Lewis acids such as HCl, HBr, and $H_2SO_4$, $BF_3.Et_2O$, p-toluenesulfonic acid (p-TsOH), trifluoroacetic acid (TFA), acetic acid, and $SnCl_4$.

Step 5' is conducted as described above for the preparation of compounds of formula I.

The compounds obtained can be recovered and purified by conventional methods, e.g., extraction, chromatography and crystallization.

The compounds of formula I can be converted to compounds having the formula VIII

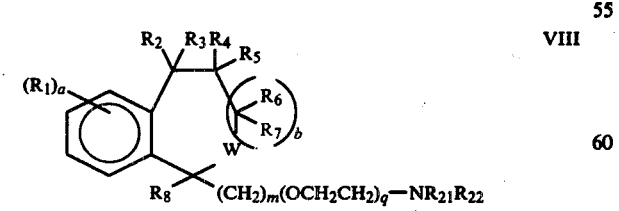

VIII wherein a, b, m, W and $R_1$ through $R_8$ are the same as above; q is one to three and $R_{21}$ and $R_{22}$ can be the same or different and are selected from the group consisting of H, alkyl of one through four carbons, and together with the N to which they are attached form heterocyclic rings of four to six ring atoms, morpholine, and $NR_9R_{10}$, wherein $NR_9R_{10}$ is a heterocyclic amine selected from the group consisting of

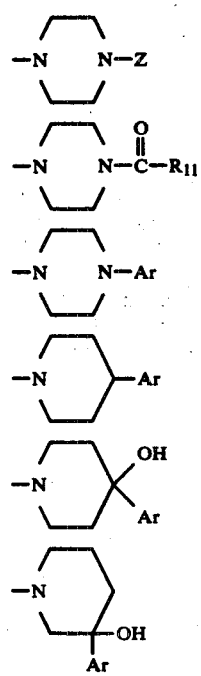

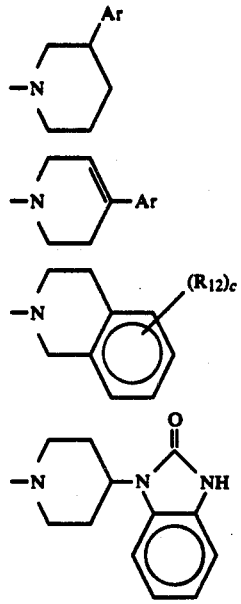

and
—NHCH₂CH₂Ar' wherein $R_{11}$ is alkyl of one through four carbons, 2-furyl, Ar, or alkoxy of one to three carbon atoms, inclusive, Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive;

$R_{12}$ is alkyl or alkoxy of one through three carbons, hydroxy, halo, or trihalomethyl.

c is zero through two;

Ar and Ar' are phenyl unsubstituted or substituted with one through three substituents selected from the group consisting of alkyl or alkoxy of one through three carbons, hydroxy, halo, and trihaloalkyl or trihaloalkoxy of one or two carbons, in accordance with the following flow chart:

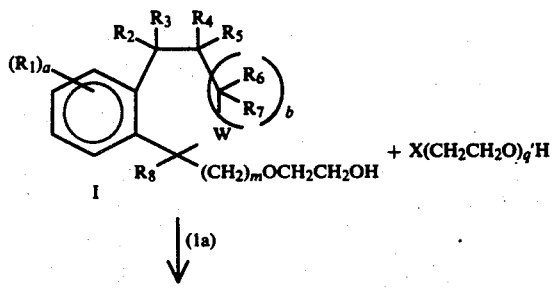

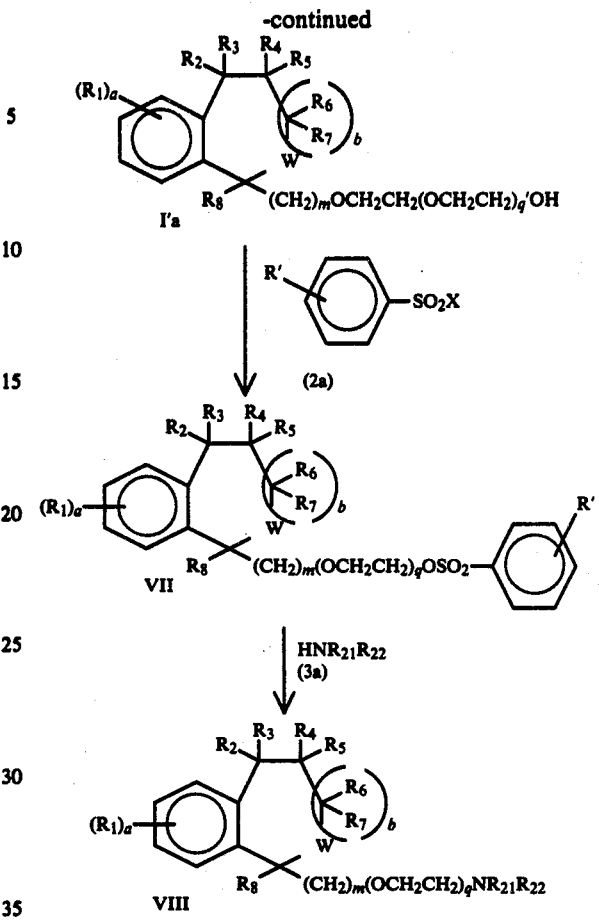

wherein X, a, b, m, q, $R_1$ through $R_8$, $R_{21}$ and $R_{22}$ are the same as defined above, q' is one or two, and R' is selected from the group consisting of alkyl of from one to three carbon atoms, $NO_2$, halo, and trifluoromethyl.

In step (1a) the compounds of formula I'a wherein q' is one or two can be prepared from compounds of formula I in the absence or presence of a solvent. It is desirable to use an acid acceptor and to run the reaction for about 20 to 120 hours at a temperature of 20° to 100°. Same acid acceptors as given below can be used (e.g. triethylamine, DBU).

Step 2a can be carried out in the presence or absence of a solvent at a temperature between 20° and 50° for a period of about one hour to ten hours. Solvents that may be used include DMF, THF, methylene chloride and toluene.

The preferred solvent is methylene chloride. Suitable acid acceptors include the trialkyl amines, e.g., triethylamine, inorganic salts, e.g. barium carbonate, and DBU. The preferred acid acceptor is triethylamine.

Step 3a is conducted by using about 1–10 moles of amine to about 1 mole of the compound of formula VII, preferably two moles of amine to about one mole of the compound of formula VII. The reaction is conducted at a temperature of about 20° to 70° for a period of one to 40 hours.

Compounds of Formula I'a and VIII can be isolated from the reaction mixtures utilizing standard methods, e.g., extraction, chromatography, crystallization and combinations thereof.

As used herein, the terms alkyl of 1–3 carbon atoms refers to methyl, ethyl, propyl, isopropyl, trihaloalkyl of 1–2 carbons is for example trifluoromethyl, trichloromethyl, 2,2,2-trifluoroethyl, alkoxy of 1–3 carbon atoms is for example methoxy, ethoxy, propoxy and isopropoxy, halo refers to chloro, bromo, fluoro, cycloalkyl of 3 through 7 carbons is for example cyclopropyl, cyclopentyl, cyclohexyl, cycloheptyl, trihaloalkoxy of 1 to 2 carbons such as 2,2,2-trifluoroethoxy, trichloromethoxy, trifluoromethoxy.

$R_1$ is o-methylenedioxy means that $R_1$ is the group

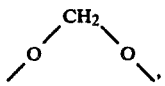

with the oxygens attached to adjacent (ortho) carbon atoms on the phenyl ring. There can be no more than one o-methylenedioxy on the free positions on the ring.

The description of this invention is not intended to be limiting for specific optically active isomers. All possible isomeric forms of the compounds are included.

In all of the procedures described herein, the desired product or intermediates can be obtained from the reaction mixture utilizing standard methods, for example, extraction, chromatography, crystallization and combinations thereof.

Pharmaceutically acceptable acid addition salts of the compounds of formula VIII are prepared by reacting the free base of a compound of the formula (VIII) with a stoichiometric amount of an acid, such as hydrogen chloride, hydrogen bromide, hydrogen iodide, sulfuric acid, phosphoric acid, acetic acid, propionic acid, butyric acid, lactic acid, citric acid, succinic acid, benzoic acid, salicyclic acid, pamoic acid, phthalic acid, cyclohexanesulfamic acid, and the like.

The compounds of formula VIII can also be formulated in unit forms for systemic administration (oral and parenteral and rectal administration) for treating hypertensive mammals, including humans. The term "dosage unit form" as used in this specification refers to physically discrete units suitable as unitary dosages for mammalian subjects, each unit containing a pre-determined quantity of the essential active ingredient, e.g., a compound (VIII) or a pharmaceutically acceptable acid addition salt thereof calculated to produce the desired effect, in combination with the required pharmaceutical means which adapt the said ingredient for systemic administration. Examples of dosage unit forms in accordance with this invention are tablets, capsules, orally administered liquid preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous vehicles which advantageously contain suspending agents, such as for example, ethanol, sodium carboxymethylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bacteristatic and fungicistatis agents; for example, parabens, chlorobutanol, benzyl alcohol, phenol, and the like. In many cases it is preferable to include isotonic agents, for example sugars or sodium chloride. Carriers and vehicles include vegetable oils, ethanol and polyols, for example, glycerol, propylene glycol, liquid polyethylene glycol, and the like. Any solid preparations for subsequent extemporaneous preparation of sterile injectable preparations are sterilized, preferably by exposure to a sterilizing gas, such as for example ethylene oxide. The aforesaid carriers, vehicles, diluents, excipients, preservatives, isotonic agents and the like constitute the pharmaceutical means which adapt the preparations for systemic administration.

For animals, food premixes with starch, oatmeal, dried fishmeat, fishmeat, fishmeal, flour, and the like can be prepared.

For CNS disease, a daily dose of 5 to 600 mg is indicated, preferentially 10 to 200 mg, in unit of two or three subdivided doses, and the exact amount is adjusted based on the weight, age, and condition of the patient.

The pharmaceutical dosage unit forms are prepared in accordance with the preceding general description to provide from about 0.5 mg to about 100 mg of the essential active ingredient (compound of formula VIII) per dosage unit form. The amount of the essential active ingredient provided in the pharmaceutical dosage unit forms is based on the finding that the effective amount of compounds prepared from compounds of this invention and acid addition salts thereof, for obtaining a hypotensive effect in mammals is within a range from about 0.1 mg per/kg to about 35 mg kg, preferably 0.3 to 15 mg/kg.

The active ingredients (formula VIII) which are prepared from the compounds of this invention can also be compounded in combination with other ingredients. The amount of such other active ingredients is to be determined with reference to the usual dosage of each such ingredient. Thus the novel compounds prepared from compounds of this invention can be combined with other hypotensive agents such as α-methyldopa (100–250 mg); with diuretics such as hydrochlorothiazide (10–50 mg); peripheral vasodilators such as hydralazine (10–100 mg); tranquilizers such as meprobamate (200–400 mg), diazepam (2–10 mg) muscle relaxants, such as carisoprodol (200–400 mg).

The tranquilization activity of the compounds of formula VIII and their pharmacologically acceptable acid addition salts are tested in mice as follows:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, and 5 cm. high), partially embedded in wood shavings, climb out in a very short time, when not treated. Mice remaining in the dish for more than 3 minutes indicates tranquilization. ED$_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than one minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e. (1) running convulsions, followed by (2) tonic extensor fits; followed by (3) deaths. Pretreatment with an active sedative or tranquilizing compound protects mice against (2) and (3).

TESTING FOR ANXIETY

Prolongation of Hypoxic survival: Pretreatment of mice exposed to the stress of progressive hypoxia and hyperapnia with anxiolytics results in a prolongation of survival. Male CF-1 derived mice are used in these studies. Thirty minutes after intraperitoneal pretreatment (test agent suspended in 0.25% methylcellulose or vehicle alone, 1 cc/100 gm body weight) the mice are placed singly in 125 ml. Erlenmeyer flasks. The receptacles are tightly stoppered and the survival time (time from stoppering to the last respiratory effort) of each animal noted. Each compound is tested at three or more doses spaced at 0.3 log intervals. Six mice are used per dose with six vehicle injected controls run simultaneously. The mean (15-18 minutes) and standard deviation (1-2 minutes) of the survival time for the vehicle treated mice are used to convert the data to a quantal form in the following manner. All survival times that differed from the mean of the controls by more than 2 standard deviations are scored as a drug effect. ED$_{50}$s are calculated by the method of Spearman and Karber (Finney, D. J., Statistical Method in Biological Assay, Hafner Publ., Co., N.Y., 1952).

The novel compounds of formula VIII and pharmacologically acceptable acid addition salts thereof also have antidepressant activity.

The main function of an anti-depressant is to return the depressed individual to normal function. This should be carefully differentiated from psychic stimulants such as the amphetamines which produced overstimulation in the normal individual.

Many different methods have been and are used to evaluate antidepressant activity. In general these methods involve antagonism to a depressant such as reserpine or tetrabenazine or a synergistic increase of the toxicity of certain compounds (i.e., yohimbine or 3,4-dihydroxyphenylalanine) and comparison of the drug action of the new compound with other known antidepressants. No single test alone can determine whether or not a new compound is an antidepressant or not, but the profile evidenced by various tests will establish that antidepressant action is present. A number of such tests are described below.

Hypothermic tests with oxotremorine
[1-[4-(pyrrolidinyl)-2-butynyl]-2-pyrrolidinone].

Oxotremorine (as well as apomorphine and tetrabenazine) produces hypothermic responses in mice. This response is blocked by anticholinergics and antidepressants such as atropine and imipramine.

Oxotremorine produced a very pronounced hypothermia which reaches a peak 60 minutes after administration. When administered at 0.6 mg/kg the body temperature of a mouse is decreased about 13° F. (when the mouse is kept at room temperature). This temperature decrease is antagonized by antidepressants, e.g., desipramine, imipramine, and amitriptyline.

The compounds of Formula VIII are tested as follows. Groups of four male mice weighing 18-22 g (Strain CF1, Carworth Farms) are injected intraperitoneally with the test compound prepared in 0.25% methylcellulose and placed in plastic cages. Thirty minutes later 1 mg/kg oxotremorine hydrochloride is injected subcutaneously. The mice are placed in a refrigerator maintained at 19° C. Thirty minutes later the intraperitoneal temperature is measured using a thermistor probe. An increase of 4° F. in the body temperature of the treated mouse (oxotremorine and test compound) over the control mouse (oxotremorine treated only) is indicative of antidepressive activity.

The same compounds were also tested for potentiation of yohimbine aggregation toxicity. The LD$_{50}$ of yohimbine hydrochloride in mice is 45 mg/kg, i.p. Administration of 20 mg/kg. of yohimbine hydrochloride is non-lethal. If an antidepressant is administered prior to the yohimbine hydrochloride (20 mg/kg) the lethality of the yohimbine hydrochloride is increased.

Eight male CF1 mice, 18-22 g are injected with yohimbine hydrochloride in saline solution. After four hours the LD$_{50}$s are determined. Groups of eight mice are injected with the antidepressant 30 minutes before the administration of yohimbine hydrochloride [YCl] (20 mg/kg). No mice or only one mouse is killed from 20 mg/kg of [YCl]. If [YCl] is administered in the presence of an antidepressant an increase in the toxicity of [YCl] is found. The ED$_{50}$ is the dosage of test compound which causes 50% of the mice to die.

Also the compounds are tested for the potentiation of apomorphine gnawing. A group of 4 mice (male, CF1, 18-22 g) are administered the test compound intraperitoneally 1 hour prior to the subcutaneous injection of apomorphine hydrochloride 10 mg/kg. The mice are then placed in a plastic box (6×11×5 inches) lined at the bottom with a cellophane-backed, absorbent paper. The degree of damage to the paper at the end of 30 minutes is scored from zero to 4. The scores 2 to 4 indicate that the compound is a potentiator of apomorphine in this test.

Results in the above tests show that the compounds of formula VIII and the pharmacologically acceptable acid addition salts thereof can be used as antidepressants, sedatives, and antianxiety drugs in mammals to achieve normalcy in the depressed or anxious individual.

As antipsychotics-neuroleptics the compounds of formula VIII and their pharmacologically acceptable acid addition salts can be used in dosages of 1-300 mg/day and preferably 5-250 mg/day in oral or injectable preparations, as described above, to alleviate psychotic states such as schizophrenia, manic depressions, etc. The exact amounts to be given are dependent on the age, weight, and condition of the patient.

The compounds of Formula VIII prepared from the compounds of this invention show potent hypotensive activity on oral administration to normotensive rats. A 4 mm Hg decrease in Mean Arterial Pressure when measured at 4 hours or 24 hours after administration of 50 mg/kg of drug is considered statistically significant.

The majority of these compounds give blood pressure drops of greater than 8 mm Hg, and some of them have the desirable feature of being of longer duration of action (beyond 24 hours).

Also, in the accepted test methodology for neuroleptic (antipsychotic) activity, such as the inhibition of amphetamine aggregation toxicity (Weaver and Kerley, J. Pharm. and Exp. Therap., 135, 240 (1962)) the dose required to inhibit death of 50% of animals previously challenged with amphetamine gives a measure of the activity of the drug; the lower the dose required, the more potent the drug. Mice are injected with the drug subcutaneously. Inhibition at a dose of 25 mg/kg is considered significant. The potent compounds of Formula VIII show a desirable level of death inhibition at a dose of 15 mg/kg or less.

In other accepted tests for antipsychotic activity, as, for example, reversal of hypothermia caused by oxotremorine again the potent compounds of formula VIII showed reversal at a dose of less than 15 mg/kg; reversal at a dose of 40 mg/kg is considered significant.

The following examples and preparations describe the manner and process of making and using the invention and set forth the best mode contemplated by the inventor of carrying out the invention but are not to be construed as limiting.

All temperatures are in degrees centigrade.

HPLC=high performance liquid chromatography.

SSB refers to Skellysolve B ®, an isomeric mixture of hexanes.

Preparation 1

7,8-Dimethoxy-1-bromomethyl-1,3,4,5-tetrahydro-2-benzoxepin

A solution of 5.00 g. of 3-(3,4-dimethoxyphenyl)-1-propanol, 9.76 ml of bromoacetaldehyde diethyl acetal, 2.0 ml of trifluoroacetic acid, and 125 ml of nitromethane is heated at 65° under a nitrogen atmosphere for 2 hours. After cooling, the reaction mixture is extracted with methylene chloride and aqueous sodium bicarbonate. The organic layer is taken to dryness in vacuo and the residue is chromatographed first with 100% methylene chloride and a second time with 10% ethyl acetate:SSB to give 300 mg of 7,8-dimethoxy-1-bromomethyl-1,3,4,5-tetrahydro-2-benzoxepin, m.p. 44°-45°.

Following the procedure of Preparation 1, but substituting the appropriate 3-(substituted-phenyl)-1-propanol, for 3-(3,4-dimethoxyphenyl)-1-propanol the 1-bromomethyl-2-benzoxepins of Table 1 can be prepared.

TABLE 1

1. 9-methoxy-8-propyl-1-bromomethyl-1,3,4,5-tetrahydro-2-benzoxepin,
2. 9-methoxy-1-bromomethyl-1,3,4,5-tetrahydro-2-benzoxepin,
3. 6,7-dimethoxy-1-bromomethyl-1,3,4,5-tetrahydro-2-benzoxepin,
4. 7-ethoxy-1-bromomethyl-1,3,4,5-tetrahydro-2-benzoxepin,
5. 7,8,9-trimethoxy-1-bromomethyl-1,3,4,5-tetrahydro-2-benzoxepin,
6. 7-hydroxy-6-methoxy-1-bromomethyl-1,3,4,5-tetrahydro-2-benzoxepin,
7. 8-bromo-7-methoxy-1-bromomethyl-1,3,4,5-tetrahydro-2-benzoxepin,
8. 7-methoxy-8,9-dichloro-1-bromomethyl-1,3,4,5-tetrahydro-2-benzoxepin,
9. 7-methoxy-8-trifluoromethyl-1-bromomethyl-1,3,4,5-tetrahydro-2-benzoxepin,
10. 7,8-methylenedioxy-1-bromomethyl-1,3,4,5-tetrahydro-2-benzoxepin,
11. 7-methoxy-5-methyl-1-bromomethyl-1,3,4,5-tetrahydro-2-benzoxepin,
12. 7,9-dimethoxy-4,5-dimethyl-1-bromomethyl-1,3,4,5-tetrahydro-2-benzoxepin,
13. 7,8,9-trimethoxy-4-methyl-1-bromomethyl-1,3,4,5-tetrahydro-2-benzoxepin,
14. 9-methoxy-4-phenyl-1-bromomethyl-1,3,4,5-tetrahydro-2-benzoxepin,
15. 7-hydroxy-5-bromo-1-bromomethyl-1,3,4,5-tetrahydro-2-benzoxepin,
16. 7,8-dimethoxy-5,5-dimethyl-1-bromomethyl-1,3,4,5-tetrahydro-2-benzoxepin,
17. 7,8-dimethoxy-4,4-dimethyl-1-bromomethyl-1,3,4,5-tetrahydro-2-benzoxepin,
18. 1-bromomethyl-7,8-dimethoxy-1,5-dihydrospiro[2-tetrahydrobenzoxepin-4(3H),1'-cyclopentane],
19. 6-bromomethyl-8,9-dipropyloxy-2,3,3a,4,6,10b-hexahydro-1H-benz[c]cyclopent[e]oxepin,
20. 4-cyclopentyl-8,9-dimethoxy-1-bromomethyl-1,3,4,5-tetrahydro-2-benzoxepin,
21. 7,8-dihydroxy-5-propyl-1-bromomethyl-1,3,4,5-tetrahydro-2-benzoxepin,
22. 7,8-dimethoxy-9-trifluoromethyl-1-bromomethyl-1,3,4,5-tetrahydro-2-benzoxepin.

Preparation 1A 7,8-Dimethoxy-1-chloroethyl-1,3,4,5-tetrahydro-2-benzoxepin

To 19.86 g. (0.149 moles) of $AlCl_3$ in 200 ml of methylene chloride is added 14.20 ml (0.149 moles) of 3-chloropropionylchloride. The mixture is stirred for 15 minutes under a nitrogen atmosphere and then 38.00 g (0.0992 moles) of the 3-chloropropionate of 3-(3,4-dimethoxyphenyl)propanol in 200 ml of methylene chloride is added over a period of 15 min. from a dropping funnel. After stirring at room temperature for 30 min., the reaction mixture is heated at reflux for an additional 3.6 hours. The reaction mixture is then cooled and aqueous sodium bicarbonate is added until gas evolution ceases. The organic layer is filtered through sodium sulfate and taken to dryness. The residue is chromatographed using 20% ethyl acetate: Skellysolve B as eluant.

A tetrahydrofuran solution of 3-chloro-4',5'-dimethoxy-3'-[3-(3-chloropropionoxy)propyl]propiophenone (about 40 g.) is added dropwise to an ice-cooled mixture of 7.3 g. of lithium aluminum hydride in tetrahydrofuran. After stirring for 20 minutes the reaction mixture is treated with 7.3 ml water, 7.3 ml 15% sodium hydroxide, and 21 ml water. The resulting suspension is filtered through Celite and the salts washed with ether. The filtrate is extracted with brine and the organic phase is filtered through sodium sulfate and concentrated.

The crude product is dissolved in 500 ml of methylene chloride and treated with 13 g of p-toluenesulfonic acid monohydrate. After stirring for 10 minutes the blue-green solution is extracted with aqueous sodium bicarbonate and brine. The organic layer is filtered through sodium sulfate and taken to dryness. Chromatography on silica gel with 20% ethyl acetate in Skellysolve B gives 14.7 g of 7,8-dimethoxy-1-chloroethyl-1,3,4,5-tetrahydro-2-benzoxepin.

Following the procedure of preparation 1A, but substituting the appropriate 3-substituted-phenylpropanol for 3-(3,4-dimethoxyphenyl)propanol, the 1-chloroethylbenzoxepins of Table 1A can be prepared.

TABLE 1A 1. 9-methoxy-8-propyl-1-chloroethyl-1,3,4,5-tetrahydro-2-benzoxepin,
2. 9-methoxy-1-chloroethyl-1,3,4,5-tetrahydro-2-benzoxepin,
3. 6,7-dimethoxy-1-chloroethyl-1,3,4,5-tetrahydro-2-benzoxepin,
4. 7-ethoxy-1-chloroethyl-1,3,4,5-tetrahydro-2-benzoxepin,
5. 7,8,9-trimethoxy-1-chloroethyl-1,3,4,5-tetrahydro-2-benzoxepin,
6. 7-hydroxy-6-methoxy-1-chloroethyl-1,3,4,5-tetrahydro-2-benzoxepin,
7. 8-bromo-7-methoxy-1-chloroethyl-1,3,4,5-tetrahydro-2-benzoxepin,
8. 7-methoxy-8,9-dichloro-1-chloroethyl-1,3,4,5-tetrahydro-2-benzoxepin,
9. 7-methoxy-8-trifluoromethyl-1-chloroethyl-1,3,4,5-tetrahydro-2-benzoxepin,
10. 7,8-methylenedioxy-1-chloroethyl-1,3,4,5-tetrahydro-2-benzoxepin,
11. 7-methoxy-5-methyl-1-chloroethyl-1,3,4,5-tetrahydro-2-benzoxepin,
12. 7,9-dimethoxy-4,5-dimethyl-1-chloroethyl-1,3,4,5-tetrahydro-2-benzoxepin,
13. 7,8,9-trimethoxy-4-methyl-1-chloroethyl-1,3,4,5-tetrahydro-2-benzoxepin,
14. 9-methoxy-4-phenyl-1-chloroethyl-1,3,4,5-tetrahydro-2-benzoxepin,
15. 7-hydroxy-5-bromo-1-chloroethyl-1,3,4,5-tetrahydro-2-benzoxepin,
16. 7,8-dimethoxy-5,5-dimethyl-1-chloroethyl-1,3,4,5-tetrahydro-2-benzoxepin,
17. 7,8-dimethoxy-4,4-dimethyl-1-chloroethyl-1,3,4,5-tetrahydro-2-benzoxepin,
18. 1-(2-chloroethyl)-1,5-dihydro-7,8-dimethoxyspiro[2-benzoxepin-4(3H), 1'-cyclopentane],
19. 6-chloroethyl-8,9-dipropyloxy-2,3,3a,4,6,10b-hexahydro-1H-benzo[c]cyclopent[e]oxepin,
20. 4-cyclopentyl-8,9-dimethoxy-1-chloroethyl-1,3,4,5-tetrahydro-2-benzoxepin,
21. 7,8-dihydroxy-5-propyl-1-chloroethyl-1,3,4,5-tetrahydro-2-benzoxepin,
22. 7,8-methoxy-9-trifluoromethyl-1-chloroethyl-1,3,4,5-tetrahydro-2-benzoxepin.

Preparation 1'

Preparation of 3-(3,4-dimethoxyphenyl)-1-propanethiol

A mixture of 5.00 g (25.5 mmoles) of 3-(3,4-dimethoxyphenyl)propanol, 1.94 g (25.5 mmoles) of thiourea, and 8.5 ml of 48% hydrobromic acid is heated on steam bath for 1 hour, allowed to stand overnight at room temperature, and then heated again on a steam bath for 2 hours. After cooling, the reaction mixture is treated with 76.5 ml of 1 M sodium hydroxide and heated on the steam bath for 1½ hours. After cooling, the reaction mixture is made acidic with 1 N hydrochloric acid and extracted with methylene chloride (followed by a brine wash). Silica gel chromatography using 10% ethyl acetate/Skellysolve B as eluent gives 0.67 g of 3-(3,4-dimethoxyphenyl)-1-propanethiol.

Following the procedure of Preparation 1', but substituting the appropriate 3-(substituted-phenyl)-1-propanol for 3-(3,4-dimethoxyphenyl)-1-propanol, the phenyl-1-propanethiols of Table 1' can be prepared.

TABLE 1'

1. 3-(4,5-methoxypropylphenyl)-1-propanethiol,
2. 3-(5-methoxyphenyl)-1-propanethiol,
3. 3-(2,3-dimethoxyphenyl)-1-propanethiol,
4. 3-(3-ethoxyphenyl)-1-propanethiol,
5. 3-(3,4,5-trimethoxyphenyl)-1-propanethiol,
6. 3-(-3-hydroxy-2-methoxyphenyl)-1-propanethiol,
7. 3-(4-bromo-3-methoxyphenyl)-1-propanethiol,
8. 3-(4,5-dichloro-3-methoxyphenyl)-1-propanethiol,
9. 3-(3-methoxy-4-trifluoromethylphenyl)-1-propanethiol,
10. 3-(3,4-methylenedioxyphenyl)-1-propanethiol,
11. 3-(3-methoxyphenyl)-3-methyl-1-propanethiol,
12. 3-(3,5-dimethoxyphenyl)-2,3-dimethyl-1-propanethiol,
13. 3-(3,4,5-trimethoxyphenyl)-2-methyl-1-propanethiol,
14. 3-(5-methoxyphenyl)-2-phenyl)-1-propanethiol,
15. 3-(3-hydroxyphenyl)-3-bromo-1-propanethiol,
16. 3-(3,4-dimethoxyphenyl)-3,3-dimethyl-1-propanethiol,
17. 3-(3,4-dimethoxyphenyl)-2,2-dimethyl-1-propanethiol,
18. 1-[(3,4-dimethoxyphenyl)methyl]cyclopent-1-yl-methanethiol,
19. 2-(3,4-dipropyloxyphenyl)cyclopent-1-yl-methanethiol,
20. 3-[(3,4-dimethoxyphenyl)-2-cyclopentyl)]-1-propanethiol,
21. 3-(3,4-dihydroxyphenyl)-3-n-propyl-1-propanethiol,
22. 3-(3,4-dimethoxy-5-trifluoromethylphenyl)-1-propanethiol, Preparation 1B 7,8-Dimethoxy-1-bromomethyl-1,3,4,5-tetrahydro-2-benzothiepin A mixture of 0.67 g of 3-(3,4-dimethoxyphenyl)-1-propanethiol, 1.0 g of bromoacetaldehyde diethylacetal, 0.16 ml of trifluoroacetic acid, and 25 ml. of nitromethane as solvent is stirred at room temperature for 1 hour, stored overnight in the freezer, and then heated at 70° for 2 hours after an additional 0.05 ml trifluoroacetic acid is added. After cooling, the reaction mixture is extracted with methylene chloride and aqueous sodium bicarbonate. The organic layer is taken to dryness, and the residue is chromatographed one time on silica gel with methylene chloride as eluent and a second time with 10% ethyl acetate/Skellysolve B as eluent to yield 7,8-dimethoxy-1-bromomethyl-1,3,4,5-tetrahydro-2-benzothiepin.

Following the procedure of preparation 1B, but substituting the appropriate 3-phenyl-1-propanethiol from Table 1' for 3-(3,4-dimethoxyphenyl)-1-propanethiol, the 1-bromomethyl-2-benzothiepins of Table 1B can be prepared.

TABLE 1B 1. 7-propyl-9-methoxy-1-bromomethyl-1,3,4,5-tetrahydro-2-benzothiepin, 2. 9-methoxy-1-bromomethyl-1,3,4,5-tetrahydro-2-benzothiepin,
3. 6,7-dimethoxy-1-bromomethyl-1,3,4,5-tetrahydro-2-benzothiepin,
4. 7-ethoxy-1-bromomethyl-1,3,4,5-tetrahydro-2-benzothiepin,
5. 7,8,9-trimethoxy-1-bromomethyl-1,3,4,5-tetrahydro-2-benzothiepin,
6. 7-hydroxy-6-methoxy-1-bromomethyl-1,3,4,5-tetrahydro-2-benzothiepin,
7. 8-bromo-7-methoxy-1-bromomethyl-1,3,4,5-tetrahydro-2-benzothiepin,
8. 8,9-dichloro-7-methoxy-1-bromomethyl-1,3,4,5-tetrahydro-2-benzothiepin,
9. 7-methoxy-8-trifluoromethyl-1-bromomethyl-1,3,4,5-tetrahydro-2-benzothiepin,
10. 7,8-methylenedioxy-1-bromomethyl-1,3,4,5-tetrahydro-2-benzothiepin,
11. 7-methoxy-5-methyl-1-bromomethyl-1,3,4,5-tetrahydro-2-benzothiepin,
12. 7,9-dimethoxy-4,5-dimethyl-1-bromomethyl-1,3,4,5-tetrahydro-2-benzothiepin,
13. 7,8,9-trimethoxy-4-methyl-1-bromomethyl-1,3,4,5-tetrahydro-2-benzothiepin,
14. 9-methoxy-4-phenyl-1-bromomethyl-1,3,4,5-tetrahydro-2-benzothiepin,
15. 7-hydroxy-5-bromo-1-bromomethyl-1,3,4,5-tetrahydro-2-benzothiepin,
16. 7,8-dimethoxy-5,5-dimethyl-1-bromomethyl-1,3,4,5-tetrahydro-2-benzothiepin,
17. 7,8-dimethoxy-4,4-dimethyl-1-bromomethyl-1,3,4,5-tetrahydro-2-benzothiepin,
18. 1-(bromomethyl)-1,5-dihydro-7,8-dimethoxyspiro[2-benzothiepin-4(3H),1'-cyclopentane]
16. 6-bromomethyl-8,9-dipropyloxy-2,3,3a,4,6,10b-hexahydro-1H-benzo[c]cyclopent[e]thiepin,
20. 4-cyclopentyl-8,9-dimethoxy-1-bromomethyl-1,3,4,5-tetrahydro-2-benzothiepin,
21. 7,8-dihydroxy-5-n-propyl-1-bromomethyl-1,3,4,5-tetrahydro-2-benzothiepin,
22. 7,8-dimethoxy-9-trifluoromethyl-1-bromomethyl-1,3,4,5-tetrahydro-2-benzoxepin,

Preparation 2

6,7-Dimethoxy-1-(2-chloroethyl)isochroman

To a solution of 3,4-dimethoxyphenethyl alcohol (110 g, 1.233 mole) and chloropropionaldehyde diethyl acetal (40 ml) in 240 ml of nitromethane, 8 ml of BF$_3$ etherate is added. The mixture is stirred for 2 hours at room temperature under nitrogen. This, after work up from water and extracting with methylene chloride gives a yellow oil. This, after column chromatography (silica gel), gives 45 g (oil) of 6,7-dimethoxy-1-(2-chloroethyl)isochroman which is crystallized from ether/pet. ether to give 41 g (70%) of 6,7-dimethoxy-1-(2-chloroethyl)isochroman as a white crystalline material, m.p. 56°–57.5°.

Analysis Calcd for: $C_{13}H_{17}ClNO_3$ C, 60.82; H, 6.68; Cl, 13.96. Found: C, 60.81; H, 6.65; Cl, 13.96.

Following the procedure of Preparation 2, but substituting the appropriate alcohol for 3,4-dimethoxyphenethyl alcohol, the 1-(2-chloroethyl)isochromans of Table 2 can be prepared.

TABLE 2

1. 8-methoxy-7-propyl-1-(2-chloroethyl)isochroman,
2. 8-methoxy-1-(2-chloroethyl)isochroman,
3. 5,6-dimethoxy-1-(2-chloroethyl)isochroman,
4. 6-ethoxy-1-(2-chloroethyl)isochroman,
5. 6,7,8-trimethoxy-1-(2-chloroethyl)isochroman,
6. 6-hydroxy-1-(2-chloroethyl)isochroman,
7. 6-methoxy-7-bromo-1-(2-chloroethyl)isochroman,
8. 6-methoxy-7,8-dichloro-1-(2-chloroethyl)isochroman,
9. 6-methoxy-7-trifluoromethyl-1-(2-chloroethyl)isochroman,
10. 6,7-methylenedioxy-1-(2-chloroethyl)isochroman,
11. 6-methoxy-4-methyl-1-(2-chloroethyl)isochroman,
12. 6,8-dimethoxy-3,4-dimethyl-1-(2-chloroethyl)-isochroman,
13. 6,7,8-trimethoxy-3-methyl-1-(2-chloroethyl)-isochroman,
14. 8-methoxy-3-phenyl-1-(2-chloroethyl)isochroman,
15. 6-hydroxy-4-bromo-1-(2-chloroethyl)isochroman,
16. 6,7-dimethoxy-4,4-dimethyl-1-(2-chloroethyl)-isochroman,
17. 6,7-dimethoxy-3,3-dimethyl-1-(2-chloroethyl)-isochroman,
18. 1-(2-chloroethyl)-6,7-dimethoxyspiro[1H-2-benzopyran-4(3H),1'-cyclopentane],
19. 5-(2-chloroethyl)-7,8-dipropyloxy-2,3,3a,5,9b-pentahydro-1H-benzo[c]cyclopent[e]pyran,
20. 3-cyclopentyl-7,8-dimethoxy-1-(2-chloroethyl)-isochroman,
21. 6,7-dihydroxy-4-n-propyl-1-(2-chloroethyl)-isochroman,
22. 6,7-dimethoxy-8-trifluoromethyl-1-(2-chloroethyl)-isochroman.

Preparation 2A 6,7-Dimethoxy-3,4-dihydro-1-(2-chloroethyl)-1H-2-benzothiopyran To a solution of 3,4-dimethoxy-phenethanethiol and chloropropionaldehyde diethyl acetal in nitromethane, BF$_3$ etherate is added. The mixture is stirred at room temperature under nitrogen. This, after work up from water, extracting with methylene chloride, on chromatography gives 6,7-dimethoxy-1-(2-chloroethyl)-1H-2-benzothiopyran.

Following the procedure of Preparation 2A, but substituting the appropriate thiol of Table 2' for 3,4-dimethoxyphenethanethiol, the 1-(2-chloroethyl)-1H-2-benzothiopyrans of Table 2A can be prepared.

TABLE 2'

1. 2-(5-methoxy-4-propylphenyl)-1-ethanethiol,
2. 2-(5-methoxyphenyl)-1-ethanethiol,
3. 2-(2,3-dimethoxyphenyl)-1-ethanethiol,
4. 2-(3-ethoxyphenyl)-1-ethanethiol,
5. 2-(3,4,5-trimethoxyphenyl)-1-ethanethiol,
6. 2-(3-hydroxy-2-methoxyphenyl)-1-ethanethiol,
7. 2-(3-methoxy-4-bromophenyl)-1-ethanethiol,
8. 2-(3-methoxy-4,5-dichlorophenyl)-1-ethanethiol,
9. 2-(3-methoxy-4-trifluoromethylphenyl)-1-ethanethiol,
10. 2-(3,4-methylenedioxyphenyl)-2-ethanethiol,
11. 2-(3-methoxyphenyl)-2-methyl-1-ethanethiol,
12. 2-(3,5-dimethoxyphenyl)-1,2-dimethyl-1-ethanethiol,
13. 2-(3,4,5-trimethoxyphenyl)-2-methyl-1-ethanethiol,
14. 2-(5-methoxyphenyl)-2-phenyl-1-ethanethiol,
15. 2-(3-hydroxyphenyl)-2-bromo-1-ethanethiol, 16. 2-(3,4-dimethoxyphenyl)-2,2-dimethyl-1-ethanethiol,
17. 2-(3,4-dimethoxyphenyl)-1,1-dimethyl-1-ethanethiol,
18. [1-(3,4-dimethoxyphenyl)cyclopent-1-yl]methanethiol,
19. 2-(3,4-dipropyloxyphenyl)cyclopentan-1-thiol,
20. 2-(3,4-dimethoxyphenyl)-2-cyclopentyl-1-ethanethiol,
21. 2-(3,4-dimethoxyphenyl)-2-n-propyl-1-ethanethiol,
22. 2-(3,4-dimethoxy-5-trifluoromethylphenyl)-1-ethanethiol.

TABLE 2A 1. 8-methoxy-7-propyl-1-(2-chloroethyl)-1H-2-benzothiopyran,
2. 8-methoxy-1-(2-chloroethyl)-1H-2-benzothiopyran,
3. 5,6-dimethoxy-1-(2-chloroethyl)-1H-2-benzothiopyran,
4. 6-ethoxy-1-(2-chloroethyl)-1H-2-benzothiopyran,
5. 6,7,8-trimethoxy-1-(2-chloroethyl)-1H-2-benzothiopyran,
6. 6-hydroxy-1-(2-chloroethyl)-1H-2-benzothiopyran,
7. 6-methoxy-7-bromo-1-(2-chloroethyl)-1H-2-benzothiopyran,
8. 6-methoxy-7,8-dichloro-1-(2-chloroethyl)-1H-2-benzothiopyran,
9. 6-methoxy-7-trifluoromethyl-1-(2-chloroethyl)-1H-2-benzothiopyran,
10. 6,7-methylenedioxy-1-(2-chloroethyl)-1H-2-benzothiopyran,
11. 6-methoxy-4-methyl-1-(2-chloroethyl)-1H-2-benzothiopyran,
12. 6,8-dimethoxy-3,4-dimethyl-1-(2-chloroethyl)-1H-2-benzothipyran,
13. 6,7,8-trimethoxy-1-(2-chloroethyl)-1H-2-benzothiopyran,
14. 8-methoxy-3-phenyl-1-(2-chloroethyl)-1H-2-benzothiopyran,
15. 6-hydroxy-4-bromo-1-(2-chloroethyl)-1H-2-benzothiopyran,
16. 6,7-dimethoxy-4,4-dimethyl-1-(2-chloroethyl)-1H-2-benzothiopyran,
17. 6,7-dimethoxy-3,3-dimethyl-1-(2-chloroethyl)-1H-2-benzothiopyran,
18. 1-(2-chloroethyl)-6,7-dimethoxyspiro[1H-2-benzothiopyran-4-(3H),1'-cyclopentane],
19. 5-(2-chloroethyl)-7,8-dipropoxy-2,3,3a,5,9b-pentahydro-1H-benzo[c]cyclopent[e]thiopyran,
20. 3-cyclopentyl-7,8-dimethoxy-1-(2-chloroethyl)-1H-2-benzothiopyran,
21. 6,7-dihydroxy-4-n-propyl-1-(2-chloroethyl)-1H-2-benzothiopyran,
22. 6,7-dimethoxy-8-trifluoromethyl-1-(2-chloroethyl)-1H-2-benzothiopyran.

Preparation 2B 2,2-Dimethyl-2-(3,4-dimethoxyphenyl)ethanol

Lithium diisopropylamine (0.0057 m) is generated at −70° from nBuLi and diisopropylamine in THF and is added to a solution of 1.00 g. (0.0048 m) of ethyl 3,4-dimethoxyphenylacetate in 20 ml of dry THF. The reaction is stirred under nitrogen at −70° for 30 min. Methyl iodide (0.67 g, 0.0048 m) is injected. After 1 hour, another 0.0057 moles of lithium diisopropylamine is added, the reaction is stirred for 30 min., and methyliodide (0.67 g, 0.0048 m) is added. The reaction is warmed to room temperature over three hours. The mixture is partitioned between methylene chloride and aqueous sodium bicarbonate. The organic phase is dried (sodium sulfate) and concentrated to yield 1.2 g of tan crystalline ethyl 2,2-dimethyl-(3,4-dimethoxyphenyl)acetate. This material is dissolved in 50 ml of 4:1 ether/tetrahydrofuran. Lithium aluminum hydride (0.20 g) is added and the mixture is stirred and refluxed for 1.5 hrs. Water (0.2 ml), 15% aqueous sodium hydroxide (0.2 m), and water (0.6 ml) are sequentially added. The mixture is filtered through sodium sulfate and then partitioned between aqueous sodium carbonate and methylene chloride. The organic phase is dried (sodium sulfate) and concentrated to yield 1.01 g of white crystalline 2,2-dimethyl-2-(3,4-dimethoxyphenyl)ethanol.

Preparation 2B'

6,7-Dimethoxy-1-bromomethylisochroman.

A mixture of 29.1 g. of 3,4-dimethoxyphenylethanol, 35 ml of bromoacetaldehyde dimethyl acetal and 5 ml of 48% HBr is stirred at 80° for 1.5 hr. The organic phase is mixed with 200 ml of methylene chloride and washed with water and then with 200 ml of 10% aqueous potassium carbonate. The organics are dried over sodium sulfate and chromatographed over silica gel. The product is crystallized from ether to yield 36.3 g. of the white solid, 70°–80°.

Preparation 2B''

4,4-Dimethyl-6,7-dimethoxy-1-bromomethylisochroman.

A 2,2-Dimethyl-2-(3,4-dimethoxyphenyl)ethanol (0.95 g, 0.0045 m) is stirred with 1.07 g (0.0054 m) of the ethyl acetal of bromoacetaldehyde and 0.19 g (0.0014 m) of BF$_3$ etherate in 25 ml of nitromethane for 15 hours. The mixture is partitioned between methylene chloride and aqueous sodium carbonate. The organic phase is dried over sodium sulfate and concentrated to yield 1.52 g of 4,4-dimethyl-6,7-dimethoxy-1-bromomethylisochroman. The nmr is consistent with the assigned structure.

Following the procedures of Preparations 2B and 2B', but substituting the appropriate alcohols for 3,4-dimethoxyphenethyl alcohol, the 1-bromomethylisochromans of Table 2B' can be prepared.

TABLE 2B'

1. 8-methoxy-7-n-propyl-1-bromomethylisochroman,
2. 8-methoxy-1-bromomethylisochroman,
3. 5,6-dimethoxy-1-bromomethylisochroman,
4. 6-ethoxy-1-bromomethylisochroman,
5. 6,7,8-trimethoxy-1-bromomethylisochroman,
6. 6-hydroxy-1-bromomethylisochroman,
7. 6-methoxy-7-bromo-1-bromomethylisochroman,
8. 6-methoxy-7,8-dichloro-1-bromomethylisochroman,
9. 6-methoxy-7-trifluoromethyl-1-bromomethylisochroman,
10. 6,7-methylenedioxy-1-bromomethylisochroman,
11. 6-methoxy-4-methyl-1-bromomethylisochroman,
12. 6,8-dimethoxy-3,4-dimethyl-1-bromomethylisochroman,
13. 6,7,8-trimethoxy-1-bromomethylisochroman,
14. 8-methoxy-3-phenyl-1-bromomethylisochroman,
15. 6-hydroxy-4-bromo-1-bromomethylisochroman,
16. 6,7-dimethoxy-4,4-dimethyl-1-bromomethylisochroman, 17. 6,7-dimethoxy-3,3-dimethyl-1-bromomethylisochroman,
18. 1-bromomethyl-6,7-dimethoxyspiro[1H-2-benzopyran-4(3H),1'-cyclopentane],
19. 5-bromomethyl-7,8-dipropoxy-2,3,3a,5,9b-pentahydro-1H-benzo[c]cyclopent[e]pyran,
20. 3-cyclopentyl-7,8-dimethoxy-1-bromomethylisochroman,
21. 6,7-dihydroxy-4-n-propyl-1-bromomethylisochroman,
22. 6,7-dimethoxy-8-trifluoromethyl-1-bromomethylisochroman,

Preparation 2C 6,7-Dimethoxy-1-bromomethyl-3,4-dihydro-1H-2-benzothiopyran.

A mixture of 3,4-dimethoxyphenylethane thiol, bromoacetaldehyde dimethylacetal, and BF₃.etherate in nitromethane is stirred at 40°. The product is dissolved in methylene chloride and washed with aqueous sodium bicarbonate. Chromatography on silica gel is used to isolate the product.

Following the procedure of Preparation 2C, but substituting the appropriate thiols for 3,4-dimethoxyphenylethane thiol, the 1-bromomethyl-3,4-dihydro-1H-2-benzothiopyrans of Table 2C can be prepared.

TABLE 2C 1. 8-methoxy-7-n-propyl-1-bromomethyl-3,4-dihydro-1H-2-benzothiopyran,
2. 8-methoxy-1-bromomethyl-3,4-dihydro-1H-2-benzothiopyran,
3. 5,6-dimethoxy-1-bromomethyl-3,4-dihydro-1H-2-benzothiopyran,
4. 6-ethoxy-1-bromomethyl-3,4-dihydro-1H-2-benzothiopyran,
5. 6,7,8-trimethoxy-1-bromomethyl-3,4-dihydro-1H-2-benzothiopyran,
6. 6-hydroxy-1-bromomethyl-3,4-dihydro-1H-2-benzothiopyran,
7. 6-methoxy-7-bromo-1-bromomethyl-3,4-dihydro-1H-2-benzothiopyran,
8. 6-methoxy-7,8-dichloro-1-bromomethyl-3,4-dihydro-1H-2-benzothiopyran,
9. 6-methoxy-7-trifluoromethyl-1-bromomethyl-3,4-dihydro-1H-2-benzothiopyran,
10. 6,7-methylenedioxy-1-bromo-3,4-dihydro-1H-2-benzothiopyran,
11. 6-methoxy-4-methyl-1-bromomethyl-3,4-dihydro-1H-2-benzothiopyran,
12. 6,8-dimethoxy-3,4-dimethyl-1-bromomethyl-3,4-dihydro-1H-2-benzothiopyran,
13. 6,7,8-trimethoxy-1-bromomethyl-3,4-dihydro-1H-2-benzothiopyran,
14. 8-methoxy-3-phenyl-1-bromomethyl-3,4-dihydro-1H-2-benzothiopyran,
15. 6-hydroxy-4-bromo-1-bromomethyl-3,4-dihydro-1H-2-benzothiopyran,
16. 6,7-dimethoxy-4,4-dimethyl-1-bromomethyl-3,4-dihydro-1H-2-benzothiopyran,
17. 6,7-dimethoxy-3,3-dimethyl-1-bromomethyl-3,4-dihydro-1H-2-benzothiopyran,
18. 1-(bromomethyl)-6,7-dimethoxyspiro[1H-2-benzothiopyran-4(3H),1'-cyclopentane],
19. 5-bromomethyl-7,8-dipropoxy-2,3,3a,5,9b-pentahydro-1H-benzo[c]cyclopent[e]thiopyran,
20. 3-cyclopentyl-7,8-dimethoxy-1-bromomethyl-3,4-dihydro-1H-2-benzothiopyran,
21. 6,7-dihydroxy-b 4-n-propyl-1-bromomethyl-3,4-dihydro-1H-2-benzothiopyran,
22. 6,7-dimethoxy-8-trifluoromethyl-1-bromomethyl-3,4-dihydro-1H-2-benzothiopyran.

Preparation 3

1-(3-chloropropyl)-6,7-dimethoxy-1-methyl-isochroman.

A mixture of 3,4-dimethoxyphenylethyl alcohol (1.72 g, 0.01 mole), 5-chloro-2-pentanone ethylene ketal (1.64 g, 0.01 mole) and 0.5 ml of BF₃ etherate in 20 ml of nitromethane is stirred at room temperature under nitrogen for 4 hours. The reaction mixture is then poured into cold water and extracted with methylene chloride. The methylene chloride solution is washed with water, dried (sodium sulfate) and concentrated to an oil. The oil is chromatographed on silica gel with 10% ethylacetate/Skellysolve B as eluate to give 40 g (54% yield) of 1-(3-chloropropyl)-6,7-dimethoxy-1-methylisochroman as a white crystalline product, m.p. 77°–69° C. The nmr of the product is consistent with the structure.

Following the procedure of Preparation 3, but substituting the appropriate alcohol for 3,4-dimethoxyphenethyl alcohol, the 1-(3-chloropropyl)-1-methylisochromans of Table 3 can be prepared.

TABLE 3

1. 8-methoxy-7-n-propyl-1-methyl-1-(3-chloropropyl)isochroman,
2. 8-methoxy-1-methyl-1-(3-chloropropyl)isochroman,
3. 5,6-dimethoxy-1-methyl-1-(3-chloropropyl)isochroman,
4. 6-ethoxy-1-methyl-1-(3-chloropropyl)isochroman,
5. 6,7,8-trimethoxy-1-methyl-1-(3-chloropropyl)isochroman,
6. 6-hydroxy-1-methyl-1-(3-chloropropyl)isochroman,
7. 6-methoxy-7-bromo-1-methyl-1-(3-chloropropyl)isochroman,
8. 6-methoxy-7,8-dichloro-1-methyl-1-(3-chloropropyl)isochroman,
9. 6-methoxy-7-trifluoromethyl-1-methyl-1-(3-chloropropyl)isochroman,
10. 6,7-methylenedioxy-1-methyl-1-(3-chloropropyl)isochroman,
11. 6-methoxy-4-methyl-1-methyl-1-(3-chloropropyl)isochroman,
12. 6,8-dimethoxy-3,4-dimethyl-1-methyl-1-(3-chloropropyl)isochroman,
13. 6,7,8-trimethoxy-1-methyl-1-(3-chloropropyl)isochroman,
14. 8-methoxy-3-phenyl-1-methyl-1-(3-chloropropyl)isochroman,
15. 6-hydroxy-4-bromo-1-methyl-1-(3-chloropropyl)isochroman,
16. 6,7-dimethoxy-4,4-dimethyl-1-methyl-1-(3-chloropropyl)isochroman,
17. 6,7-dimethoxy-3,3-dimethyl-1-methyl-1-(3-chloropropyl)isochroman,
18. 1-methyl-1-(3-chloropropyl)-6,7-dimethoxyspiro[1H-2-benzopyran-4(3H),1'-cyclopentane],
19. 5-methyl-5-(3-chloropropyl)-7,8-dipropoxy-2,3,3a,5,9b-pentahydro-1H-benzo[c]cyclopent[e]pyran, 20. 3-cyclopentyl-7,8- dimethoxy-1-methyl-1-(3-chloropropyl)isochroman,
21. 6,7-dihydroxy-4-n-propyl-1-methyl-1-(3-chloropropyl)isochroman,
22. 6,7-dimethoxy-8-trifluoromethyl-1-methyl-1-(3-chloropropyl)isochroman.

Preparation 3A 1-(3-Chloropropyl)-3,4-dihydro-6,7-dimethoxy-1-methyl-1H-2-benzothiopyran.

A mixture of 3,4-dimethoxyphenylethanethiol, 5-chloro-2-pentanone ethylene ketal and $BF_3$ etherate in nitromethane is stirred under $N_2$. The reaction mixture is then poured into cold water and extracted with methylene chloride. The methylene chloride solution is washed with water, dried, (sodium sulfate) and concentrated. Column chromatography of the concentrate gives 1-(3-chloropropyl)-3,4-dihydro-6,7-dimethoxy-1-methyl-1H-2-benzothiopyran.

Following the procedure of Preparation 3A, but substituting the appropriate thiol for 3,4-dimethoxyphenylethanethiol, the 1-(3-chloropropyl)-3,4-dihydro-6,7-dimethoxy-1-methyl-1H-2-benzothiopyrans of Table 3A can be prepared.

TABLE 3A 1. 8-methoxy-7-n-propyl-1-(3-chloropropyl)-1-methyl-3,4-dihydro-1H-2-benzothiopyran,
2. 8-methoxy-1-(3-chloropropyl)-1-methyl-3,4-dihydro-1H-2-benzothiopyran,
3. 5,6-dimethoxy-1-(3-chloropropyl)-1-methyl-3,4-dihydro-1H-2-benzothiopyran,
4. 6-ethoxy-1-(3-chloropropyl)-1-methyl-3,4-dihydro-1H-2-benzothiopyran,
5. 6,7,8-trimethoxy-1-(3-chloropropyl)-1-methyl-3,4-dihydro-1H-2-benzothiopyran,
6. 6-hydroxy-1-(3-chloropropyl)-1-methyl-3,4-dihydro-1H-2-benzothiopyran,
7. 6-dimethoxy-7-bromo-1-(3-chloropropyl)-1-methyl-3,4-dihydro-1H-2-benzothiopyran,
8. 6-methoxy-7,8-dichloro-1-(3-chloropropyl)-1-methyl-3,4-dihydro-1H-2-benzothiopyran,
9. 6-methoxy-7-trifluoromethyl-1-(3-chloropropyl)-1-methyl-3,4-dihydro-1H-2-benzothiopyran,
10. 6,7-methylenedioxy-1-(3-chloropropyl)-1-methyl-3,4-dihydro-1H-2-benzothiopyran,
11. 6-methoxy-4-methyl-1-(3-chloropropyl)-1-methyl-3,4-dihydro-1H-2-benzothiopyran,
12. 6,8-dimethoxy-3,4-dimethyl-1-(3-chloropropyl)-1-methyl-3,4-dihydro-1H-2-benzothiopyran,
13. 6,7,8-trimethoxy-1-(3-chloropropyl)-1-methyl-3,4-dihydro-1H-2-benzothiopyran,
14. 8-methoxy-3-phenyl-1-(3-chloropropyl)-1-methyl-3,4-dihydro-1H-2-benzothiopyran,
15. 6-hydroxy-4-bromo-1-(3-chloropropyl)-1-methyl-3,4-dihydro-1H-2-benzothiopyran,
16. 6,7-dimethoxy-4,4-dimethyl-1-(3-chloropropyl)-1-methyl-3,4-dihydro-1H-2-benzothiopyran,
17. 6,7-dimethoxy-3,3-dimethyl-1-(3-chloropropyl)-1-methyl-3,4-dihydro-1H-2-benzothiopyran,
18. 1-methyl-1-(3-chloropropyl)-6,7-dimethoxyspiro[1H-2-benzothiopyran-4(3H),1'-cyclopentane,
19. 1-methyl-1-(3-chloropropyl)-7,8-dipropoxy-2,3,3a,5,9b-pentahydro-1H-benzo[c]cyclopent[e]thiopyran,
20. 3-cyclopentyl-7,8-dimethoxy-1-methyl-1-(3-chloropropyl)-3,4-dihydro-1H-2-benzothiopyran,
21. 6,7-dihydroxy-4-n-propyl-1-(3-chloropropyl)-1-methyl-3,4-dihydro-1H-2-benzothiopyran,
22. 6,7-dimethoxy-8-trifluoromethyl-1-(3-chloropropyl)-1-methyl-3,4-dihydro-1H-2-benzothiopyran.

Preparation 4

Following the procedures of Preparations 1-3 but substituting the appropriate halo-substituted ketone or aldehydes from Table 4' the following 1-halo-alkyl benzoxepins wherein the alkyl group is $(CH_2)_3$ can be prepared brom 3-(3,4-dimethoxyphenyl)propanol.

TABLE 4

1. 7,8-dimethoxy-1-[3-chloropropyl]-1,3,4,5-tetrahydro-2-benzoxepin,
2. 7,8-dimethoxy-1-[3-chloropropyl]-1-methyl-1,3,4,5-tetrahydro-2-benzoxepin,
3. 7,8-dimethoxy-1-[3-chloropropyl]-1-(4'-fluorophenyl)-1,3,4,5-tetrahydro-2-benzoxepin, The compounds of Table 4 are derived from the aldehyde or ketones of Table 4' and 3-(3,4-dimethoxyphenyl)propanol.

TABLE 4'

1. methyl 3-chloropropyl ketone,
2. 4-chlorobutanol,
3. 4-fluorophenyl 3-chloropropyl ketone.

Similarly, from the alcohols which are used to prepare the benzoxepins of Table 1 and the appropriate halo-substituted ketones or aldehydes (Table 4') and following the procedures of Preparations 1-3, the benzoxepins which are analogous to those of Table 4 can be prepared.

Preparation 5

2-[(1,3,4,5-Tetrahydro-7,8-dimethoxy-2-benzoxepin-1-yl)methoxy]ethyl chloride

A mixture of 10.33 g (0.343 moles) of 1-bromomethyl-1,3,4,5-tetrahydro-7,8-dimethoxy-2-benzoxepin, 10 ml of 2-chloroethanol, and 6.77 g of barium carbonate is stirred at 90° for 46 hours. The reaction mixture is then cooled, ethanol is added, and the solids are removed by filtration. The filtrate is taken to dryness in vacuo and the resulting oil is extracted with methylene chloride and aqueous sodium bicarbonate. The organic layer is then taken to dryness and chromatographed on silica gel using 10% ethylacetate:Skellysolve B as eluent to give 4.18 g (41%) of 2-[(1,3,4,5-tetrahydro-7,8-dimethoxy-2-benzoxepin-1-yl)-methoxy]ethyl chloride, m.p. 90°-91°.

Analysis Calc'd for: $C_{15}H_{21}ClO_4$: C, 59.89; H, 7.04. Found: C, 60.06; H, 7.57.

Following the procedure of Preparation 5, but substituting the appropriate 1-bromomethyl-2-benzoxepin from Table 1 for 1-bromomethyl-7,8-dimethoxybenzoxepin, and chloroethanol the 2-[(1,3,4,5-tetrahydro-2-benzoxepin-1-yl)methoxy]ethyl chlorides of Table 5 can be prepared.

TABLE 5

1. 2-[(9-methoxy-8-propyl-1,3,4,5-tetrahydro-2-benzoxepin-1-yl)methoxy]ethyl chloride,
2. 2-[(2-methoxy-1,3,4,5-tetrahydro-2-benozoxepin-1-yl)methoxy]ethyl chloride,
3. 2-[(6,7-dimethoxy-1,3,4,5-tetrahydro-2-benzoxepin-1-yl)methoxy]ethyl chloride, 4. 2-[(7-ethoxy-1,3,4,5-tetrahydro-2-benzoxepin-1-yl)methoxy]ethyl chloride,
5. 2-[(7,8,9-trimethoxy-1,3,4,5-tetrahydro-2-benzoxepin-1-yl)methoxy]ethyl chloride,
6. 2-[(7-hydroxy-6-methoxy-1,3,4,5-tetrahydro-2-benzoxepin-1-yl)methoxy]ethyl chloride,
7. 2-[(8-bromo-7-methoxy-1,3,4,5-tetrahydro-2-benzoxepin-1-yl)methoxy]ethyl chloride,
8. 2-[(7-methoxy-8,9-dichloro-1,3,4,5-tetrahydro-2-benzoxepin-1-yl)methoxy]ethyl chloride,
9. 2-[(7-methoxy-8-trifluoromethyl-1,3,4,5-tetrahydro-2-benzoxepin-1yl)methoxy]ethyl chloride,
10. 2-[(7,8-methylenedioxy-1,3,4,5-tetrahydro-2-benzoxepin-1-yl)methoxy]ethyl chloride,
11. 2-[(7-methoxy-5-methyl-1,3,4,5-tetrahydro-2-benzoxepin-1-yl)methoxy]ethyl chloride,
12. 2-[(7,9-dimethoxy-4,5-dimethyl-1,3,4,5-tetrahydro-2-benzoxepin-1-yl)methoxy]ethyl chloride,
13. 2-[(7,8,9-trimethoxy-4-methyl-1,3,4,5-tetrahydro-2-benzoxepin-1-yl)methoxy]ethyl chloride,
14. 2-[(9-methoxy-4-phenyl-1,3,4,5-tetrahydro-2-benzoxepin-1-yl)methoxy]ethyl chloride,
15. 2-[(7-hydroxy-5-bromo-1,3,4,5-tetrahydro-2-benzoxepin-1-yl)methoxy]ethyl chloride,
16. 2-[(7,8-dimethoxy-5,5-dimethyl-1,3,4,5-tetrahydro-2-benzoxepin-1-yl)methoxy]ethyl chloride,
17. 2-[(7,8-dimethoxy-4,4-dimethyl-1,3,4,5-tetrahydro-2-benzoxepin-1-yl)methoxy]ethyl chloride,
18. 1-(2-chloroethoxymethyl)-1,5-dihydro-7,8-dimethoxyspiro[2-benzoxepin-4(3H),1'-cyclopentane],
19. 6-(2-chloroethoxymethyl)-8,9-dipropoxy-2,3,3a,4,6,10b-hexahydro-1H-benzo[c]cyclopent[e]oxepin,
20. 2-[(4-chloropentyl-8,9-dimethoxy-1,3,4,5-tetrahydro-2-benzoxepin-1-yl)methoxy]ethyl chloride,
21. 2-[(7,8-dihydroxy-5-propyl-1,3,4,5-tetrahydro-2-benzoxepin-1-yl)methoxy]ethyl chloride,
22. 2-[(7,8-dimethoxy-9-trifluoromethyl-1,3,4,5-tetrahydro-2-benzoxepin-1-yl)methoxy]ethyl chloride.

Similarly from chloroethanol and the appropriate 1-chloroethylbenzoxepins of Table 1A or the 1-chloropropylbenzoxepins of Table 4a, and following the procedure of preparation 5, the analogous 2-[(1,3,4,5-tetrahydro-2-benzoxepin-1-yl)alkoxy]ethyl chlorides can be prepared.

Preparation 5a

2-[(1,3,4,5-tetrahydro-7,8-dimethoxy-2-benzothiepin-1-yl)methoxy]ethyl chloride.

A mixture of 1-bromomethyl-7,8-dimethoxybenzothiepin, 2-chloroethanol, and barium carbonate is stirred at 40°–90° for 10–60 hours. The reaction mixture is then cooled, ethanol is added, and the solids are removed by filtration. The filtrate is taken to dryness in vacuo and the resulting oil is extracted with methylene chloride and aqueous sodium bicarbonate. The organic layer is then taken to dryness and chromatographed on silica gel to give 2-[(1,3,4,5-tetrahydro-7,8-dimethoxy-2-benzothiepin-1-yl)methoxy]ethyl chloride.

Following the procedure of Preparation 5a, but substituting the appropriate 1-halomethyl-benzothiepin for 1-bromomethyl-7,8-dimethoxybenzothiepin the 2-[(1,3,4,5-tetrahydro-2-benzothiepin-1-yl)methoxy]ethyl chlorides (in Table 5a) can be prepared.

TABLE 5a 1. 2-[(9-methoxy-8-propyl-1,3,4,5-tetrahydro-2-benzothiepin-1-yl)methoxy]ethyl chloride,
2. 2-[(9-methoxy-1,3,4,5-tetrahydro-2-benzothiepin-1-yl)methoxy]ethyl chloride,
3. 2-[(6,7-dimethoxy-1,3,4,5-tetrahydro-2-benzothiepin-1-yl)methoxy]ethyl chloride,
4. 2-[(7-ethoxy-1,3,4,5-tetrahydro-2-benzothiepin-1-yl)methoxy]ethyl chloride,
5. 2-[(7,8,9-trimethoxy-1,3,4,5-tetrahydro-2-benzothiepin-1-yl)methoxy]ethyl chloride,
6. 2-[(7-hydroxy-6-methoxy-1,3,4,5-tetrahydro-2-benzothiepin-1-yl)methoxy]ethyl chloride,
7. 2-[(8-bromo-7-methoxy-1,3,4,5-tetrahydro-2-benzothiepin-1-yl)methoxy]ethyl chloride,
8. 2-[(7-methoxy-8,9-dichloro-1,3,4,5-tetrahydro-2-benzothiepin-1-yl)methoxy]ethyl chloride,
9. 2-[(7-methoxy-8-trifluoromethyl-1,3,4,5-tetrahydro-2-benzothiepin-1-yl)methoxy]ethyl chloride,
10. 2-[(7,8-methylenedioxy-1,3,4,5-tetrahydro-2-benzothiepin-1-yl)mdthoxy]ethyl chloride,
11. 2-[(7-methoxy-5-methyl-1,3,4,5-tetrahydro-2-benzothiepin-1-yl)methoxy]ethyl chloride,
12. 2-[(7,9-dimethoxy-4,5-dimethyl-1,3,4,5-tetrahydro-2-benzothiepin-1-yl)methoxy]ethyl chloride,
13. 2-[(7,8,9-trimethoxy-4-methyl-1,3,4,5-tetrahydro-2-benzothiepin-1-yl)methoxy]ethyl chloride,
14. 2-[(9-methoxy-4-phenyl-1,3,4,5-tetrahydro-2-benzothiepin-1-yl)methoxy]ethyl chloride,
15. 2-[(7-hydroxy-5-bromo-1,3,4,5-tetrahydro-2-benzothiepin-1-yl)methoxy]ethyl chloride,
16. 2-[(7,8-dimethoxy-5,5-dimethyl-1,3,4,5-tetrahydro-2-benzothiepin-1-yl)methoxy]ethyl chloride,
17. 2-[(7,8-dimethoxy-4,4-dimethyl-1,3,4,5-tetrahydro-2-benzothiepin-1-yl)methoxy]ethyl chloride,
18. 1-(2-chloroethoxymethyl)-1,5-dihydro-7,8-dimethoxyspiro[2-benzothiepin-4(3H),1'-cyclopentane],
19. 6-(2-chloroethoxymethyl)-8,9-diporpoxy-2,3,3a,4,6,10b-hexahydro-1H-benzo[c]cyclopent[e]thiepin,
20. 2-[(4-cyclopentyl-8,9-dimethoxy-1,3,4,5-tetrahydro-2-benzothiepin-1-yl)methoxy]ethyl chloride,
21. 2-[(7,8-dihydroxy-5-propyl-1,3,4,5-tetrahydro-2-benzothiepin-1-yl)methoxy]ethyl chloride,
22. 2-[(7,8-dimethoxy-9-trifluoromethyl-1,3,4,5-tetrahydro-2-benzothiepin-1-yl)methoxy]ethyl chloride.

Similarly, from chloroethanol and the appropriate 1-chloroethyl-2-benzothiepins prepared according to Preparation 1A but starting with the thiols corresponding to the alcohols or 1-chloropropyl-2-benzothiepins prepared from the thiols following Preparation 4 and following the procedure of Preparation 5a, the corresponding 2-[(1,3,4,5-tetrahydro-2-benzothiepin-1-yl)alkoxy]ethyl chlorides can be prepared.

Preparation 6

2-[7,8-dimethoxy-4,4-dimethyl-2-benzoxepin-1-yl]ethyl chloride

A. 3,4-dimethoxybenzyl bromide

To an ice-cooled solution of 37 g (0.22 moles) of 3,4-dimethoxybenzyl alcohol in 350 ml of toluene and 1400 ml of hexane is added 50 ml of 48% hydrochloric acid. After two hours the organic layer is decanted and extracted with water. The organic leyer is then filtered through anhydrous sodium sulfate ($Na_2SO_4$). The residue is shaken with hexane, leaving an oil behind. The oil is dissolved in ether and hexane is added until the solution turns cloudy. After standing overnight in the refrigerator 24 g of crystalline product is isolated. The spectral data are consistent with the subtitled product (melting point 47°–50°).

B. 3-(3,4-dimethoxyphenyl)-2,2-dimethylpropanoic acid

To a tetrahydrofuran solution of 13.45 ml (0.0953 mol) of diisopropylamine cooled in an ice/brine bath is added 59.5 ml (0.0953 mol) of n-butyllithium hexane. After stirring for five minutes, 4.00 ml (0.0433 mol) of isobutyric acid is added, followed by 7.53 ml (0.0433 mol) of hexamethylphosphoramide. The solution is stirred for three hours, after which 10.25 g (0.0444 mol) of 3,4-dimethoxybenzylbromide (from Part A) in tetrahydrofuran is slowly added. The ice/brine bath is removed and the reaction mixture allowed to come to room temperature while stirring overnight.

The reaction mixture is extracted with 7% aqueous sodium hydroxide and backwashed with ether. The basic layer is made acidic with concentrated hydrochloric acid and is then extracted with methylene chloride. The organic layer is filtered through anhydrous sodium sulfate and taken to dryness. The spectral data are consistent with the subtitled product. The compound is taken on to Part C in the crude form.

C. 3-(3,4-dimethoxyphenyl)-2,2-dimethyl-1-propanol

To the crude product, acid from part B in 300 ml methylene chloride is added 7 ml of borane methyl sulfide. After stirring for 2½ hours, water is added and the mixture extracted with aqueous sodium bicarbonate (NaHCO₃) and brine. The organic layer is concentrated, and the residue is chromatographed on silica gel with 2% methanol in methylene chloride as eluent, to give 8.4 g of subtitled product (melting point 48.5°–50.0°).

D.
2-[7,8-dimethoxy-4,4-dimethyl-2-benzoxepin-1-yl]ethyl chloride

To 4.93 g (0.022 mol) of the alcohol from part C, 5.52 ml (0.033 mol) of β-chloropropion-aldehyde diethyl acetal, and 250 ml of nitromethane is added 2.70 ml (0.022 mol) of boron trifluoride etherate. The reaction mixture is stirred at room temperature for 1¼ hours, after which it is extracted with methylene chloride followed by aqueous sodium bicarbonate and then water. The organic phase is taken to dryness in vacuo and ether is added to the residue. After standing overnight the precipitated solids are filtered off and the ether layer is chromatographed on silica gel with 20% ethyl acetate in Skellysolve B ® to give 4.2 g of title product. (m.p. 66°–67° C.)

Calc'd for $C_{16}H_{23}ClO_3$: C, 64.31; H, 7.76. Found: C, 64.49; H, 7.61.

EXAMPLE 1
2-[(1,3,4,5-Tetrahydro-7,8-dimethoxy-2-benzoxepin-1-yl)methoxy]ethanol.

A mixture of 3.67 g (12.2 mmoles) of 1-bromomethyl-7,8-dimethoxy-2-benzoxepin, 2.12 ml (12.2 mmoles) of diisopropylethylamine, and 15 ml of ethylene glycol is heated at 100° for 7 hours. The reaction mixture is then cooled and extracted with methylene chloride, then with water and finally with brine. The organic layer is filtered through sodium sulfate, taken to dryness, and chromatographed on silica gel to give 3.06 g (89%) of 2-[(1,3,4,5-tetrahydro-7,8-dimethoxy-2-benzoxepin-1-yl)methoxy] ethanol: mass spectrum: M+ (m/e=282).

Following the procedure of Example 1, but substituting the appropriate 1-halomethyl-2-benzoxepin, the 2-[(1,3,4,5-tetrahydro-2-benzoxepin-1-yl)methoxy]ethanols of Table 6 can be prepared.

TABLE 6

1. 2-[(1,3,4,5-tetrahydro-9-methoxy-8-propyl-2-benzoxepin-1-yl)methoxy]ethanol,
2. 2-[(1,3,4,5-tetrahydro-9-methoxy-2-benzoxepin-1-yl)methoxy]ethanol,
3. 2-[(1,3,4,5-tetrahydro-6,7-dimethoxy-2-benzoxepin-1-yl)methoxy]ethanol,
4. 2-[(1,3,4,5-tetrahydro-7-ethoxy-2-benzoxepin-1-yl)methoxy]ethanol,
5. 2-[(1,3,4,5-tetrahydro-7,8,9-trimethoxy-2-benzoxepin-1-yl)methoxy]ethanol,
6. 2-[(1,3,4,5-tetrahydro-7-hydroxy-6-methoxy-2-benzoxepin-1-yl)methoxy]ethanol,
7. 2-[(1,3,4,5-tetrahydro-8-bromo-7-methoxy-2-benzoxepin-1-yl)methoxy]ethanol,
8. 2-[(1,3,4,5-tetrahydro-7-methoxy-8,9-dichloro-2-benzoxepin-1-yl)methoxy]ethanol,
9. 2-[(1,3,4,5-tetrahydro-7-methoxy-8-trifluoromethyl-2-benzoxepin-1-yl)methoxy]ethanol,
10. 2-[(1,3,4,5-tetrahydro-7,8-methylenedioxy]-2-benzoxepin-1-yl)methoxy]ethanol,
11. 2-[(1,3,4,5-tetrahydro-7-methoxy-5-methyl-2-benzoxepin-1-yl)methoxy]ethanol
12. 2-[(1,3,4,5-tetrahydro-7,9-dimethoxy-4,5-dimethyl-2-benzoxepin-1-yl)methoxy]ethanol
13. 2-[(1,3,4,5-tetrahydro-7,8,9-trimethoxy-4-methyl-2-benzoxepin-1-yl)methoxy]ethanol
14. 2-[(1,3,4,5-tetrahydro-9-methoxy-4-phenyl-2-benzoxepin-1-yl)methoxy]ethanol
15. 2-[(1,3,4,5-tetrahydro-7-hydroxy-5-bromo-2-benzoxepin-1-yl)methoxy]ethanol
16. 2-[(1,3,4,5-tetrahydro-7,8-dimethoxy-5,5-dimethyl-2-benzoxepin-1-yl)methoxy]ethanol
17. 2-[(1,3,4,5-tetrahydro-7,8-dimethoxy-4,4-dimethyl-2-benzoxepin-1-yl)methoxy]ethanol
18. 2-[[1,5-dihydro-7,8-dimethoxyspiro[2-benzoxepin-4(3H)-1'-cyclopentane]-1-yl]methoxy]ethanol
19. 2-[(8,9-dipropoxy-2,3,3a,4,6,10b-hexahydro-1H-benzo[c]cyclopent[e]oxepin-6-yl)methoxy]ethanol
20. 2-[(1,3,4,5-tetrahydro-4-cyclopentyl-8,9-dimethoxy-2-benzoxepin-1-yl)methoxy]ethanol
21. 2-[(1,3,4,5-tetrahydro-7,8-dihydroxy-5-n-propyl-2-benzoxepin-1-yl)methoxy]ethanol
22. 2-[(7,8-dimethoxy-9-trifluoromethyl-1,3,4,5-tetrahydro-2-benzoxepin-1-yl)methoxy]ethanol Similarly, from ethylene glycol and the appropriate 1-chloroethyl benzoxepins of Table 1A or the 1-chloropropylbenzoxepins of Table 4, and following the procedure of Example 1, the analogous 2-[(1,3,4,5-tetrahydro-2-benzoxepin-1-yl)alkoxy]ethanols can be prepared.

EXAMPLE 2
2-[(1,3,4,5-tetrahydro-7,8-dimethoxy-2-benzothiopin-1-yl)methoxy]ethanol.

A mixture of 1-bromomethyl-7,8-dimethoxy-2-benzothiepin, diisopropylethylamine, and ethylene glycol is heated at 30° to 100° C. for 5–50 hours. The reaction mixture is then cooled, diluted with methylene chloride and extracted with water followed by brine. The organic layer is filtered through sodium sulfate, taken to dryness, and chromatographed on silica gel to give 2-[(1,3,4,5-tetrahydro-7,8-dimethoxy-2-benzothiepin-1-yl)methoxy]ethanol.

Following the procedure of Example 2, but substituting the appropriate 1-halomethyl-2-benzothiepin of Table 1B the 2-[(1,3,4,5-tetrahydro-2-benzothiepin-1-yl)methoxy]ethanols of Table 7 can be prepared.

TABLE 7

1. 2-[(1,3,4,5-tetrahydro-8-propyl-9-methoxy-2-benzothiepin-1-yl)methoxy]ethanol
2. 2-[(1,3,4,5-tetrahydro-9-methoxy-2-benzothiepinyl)methoxy]ethanol
3. 2-[(1,3,4,5-tetrahydro-6,7-dimethoxy-2-benzothiepin-1-yl)methoxy]ethanol
4. 2-[(1,3,4,5-tetrahydro-7-ethoxy-2-benzothiepin-1-yl)methoxy]ethanol
5. 2-[(1,3,4,5-tetrahydro-7,8,9-trimethoxy-2-benzothiepin-1-yl)methoxy]ethanol
6. 2-[(1,3,4,5-tetrahydro-7-hydroxy-6-methoxy-2-benzothiepin-1-yl)methoxy]ethanol
7. 2-[(1,3,4,5-tetrahydro-8-bromo-7-methoxy-2-benzothiepin-1-yl)methoxy]ethanol
8. 2-[(1,3,4,5-tetrahydro-7-methoxy-8,9-dichloro-2-benzothiepin-1-yl)methoxy]ethanol
9. 2-[(1,3,4,5-tetrahydro-7-methoxy-8-trifluoromethyl)-2-benzothiepin-1-yl)methoxy]ethanol
10. 2-[(1,3,4,5-tetrahydro-7,8-methylenedioxy-2-benzothiepin-1-yl)methoxy]ethanol
11. 1-[(1,3,4,5-tetrahydro-7-methoxy-5-methyl-2-benzothiepin-1-yl)methoxy]ethanol
12. 2-[(1,3,4,5-tetrahydro-7,9-dimethoxy-4,5-dimethyl-2-benzothiepin-1-yl)methoxy]ethanol
13. 2-[(1,3,4,5-tetrahydro-7,8,9-trimethoxy-4-methyl-2-benzothiepin-1-yl)methoxy]ethanol
14. 2-[(1,3,4,5-tetrahydro-9-methoxy-4-phenyl-2-benzothiepin-1-yl)methoxy]ethanol
15. 2-[(1,3,4,5-tetrahydro-7-hydroxy-5-bromo-2-benzothiepin-1-yl)methoxy]ethanol
16. 2-[(1,3,4,5-tetrahydro-7,8-dimethoxy-5,5-dimethyl-2-benzothiepin-1-yl)methoxy]ethanol
17. 2-[(1,3,4,5-tetrahydro-7,8-dimethoxy-4,4-dimethyl-2-benzothiepin-1-yl)methoxy]ethanol
18. 2-[1,5-dihydro-7,8-dimethoxyspiro[2-benzothiepin-4(3H)-1'-cyclopentane]-1-yl]methoxyethanol
19. 2-[(8,9-dipropoxy-2,3,3a,4,6,10b-hexahydro-1H-benzo[c]cyclopent[e]thiepin-6-yl)methoxy]ethanol
20. 2-[(1,3,4,5-tetrahydro-4-cyclopentyl-8,9-dimethoxy-2-benzothiepin-1-yl)methoxy]ethanol
21. 2-[(1,3,4,5-tetrahydro-7,8-dihydroxy-5-propyl-2-benzothiepin-1-yl)methoxy]ethanol
22. 2-[(7,8-dimethoxy-9-trifluoromethyl-1,3,4,5-tetrahydro-2-benzothiepin-1-yl)methoxy]ethanol.

Similarly, from ethylene glycol and the appropriate 1-chloroethyl-2-benzothiepins or the 1-chloropropyl-2-benzothiepins prepared according to the procedure of Preparation 1B from the desired 3-phenyl-1-propanethiols and the corresponding ketones or aldehydes (e.g. Table 4'), the analogous 2-[(1,3,4,5-tetrahydro-2-benzothiepin-1-yl)alkoxy]ethanols can be prepared with the procedure of Example 2.

EXAMPLE 3

2-[(1,3,4,5-tetrahydro-7,8-dimethoxy-2-benzoxepin-1-yl)methoxy]ethyl 4-nitrobenzene sulfonate.

To a mixture of 3.00 g. (10.6 mmoles of 2-[(1,3,4,5-tetrahydro-7,8-dimethoxy-2-benzoxepin-1-yl)methoxy]ethanol and 1.63 ml (11.7 mmoles) of triethylamine is added 2.59 g (11.7 mmoles) of p-nitrobenzenesulfonyl chloride. The reaction mixture is stirred at room temperature for 1 hour and then heated at 50° for 30 minutes. To this is added an additional 0.5 g of p-nitrobenzenesulfonyl chloride and 0.5 ml of triethylamine. After stirring at room temperature for 30 minutes, the reaction mixture is extracted with aqueous sodium bicarbonate and brine. The organic layer is filtered through sodium sulfate and taken to dryness. The residue is chromatographed on silica gel using 1% methanol methylene chloride as eluant to give 1.56 g (32%) 2-[(1,3,4,5-tetrahydro-7,8-dimethoxy-2-benzoxepin-1-yl)methoxy]ethyl 4-nitrobenzene sulfonate. The nmr spectrum was consistent with the assigned structure.

Utilizing the procedure of Example 3, but substituting the appropriate 2-[(1,3,4,5-tetrahydro-2-benzoxepin-1-yl)methoxy]ethanol, the 2-[(1,3,4,5-tetrahydro-2-benzoxepin-1-yl)methoxy]ethyl benzenesulfonates of Table 8 can be prepared.

TABLE 8

1. 2-[(1,3,4,5-tetrahydro-9-methoxy-8-propyl-2-benzoxepin-1-yl)methoxy]ethyl 4-nitrobenzenesulfonate
2. 2-[(1,3,4,5-tetrahydro-9-methoxy-2-benzoxepin-1-yl)methoxy]ethyl 4-nitrobenzenesulfonate
3. 2-[(1,3,4,5-tetrahydro-6,7-dimethoxy-2-benzoxepin-1-yl)methoxy]ethyl 4-methoxybenzenesulfonate
4. 2-[(1,3,4,5-tetrahydro-7-ethoxy-2-benzoxepin-1-yl)methoxy]ethyl 4-ethylbenzenesulfonate
5. 2-[(1,3,4,5-tetrahydro-7,8,9-trimethoxy-2-benzoxepin-1-yl)methoxy]ethyl 4-nitrobenzenesulfonate
6. 2-[(1,3,4,5-tetrahydro-7-hydroxy-6-methoxy-2-benzoxepin-1-yl)methoxy]ethyl 4-chlorobenzenesulfonate
7. 2-[(1,3,4,5-tetrahydro-8-bromo-7-methoxy-2-benzoxepin-1-yl)methoxy]ethyl 4-nitrobenzenesulfonate
8. 2-[(1,3,4,5-tetrahydro-7-methoxy-8,9-dichloro-2-benzoxepin-1-yl)methoxy]ethyl 4-nitrobenzenesulfonate
9. 2-[(1,3,4,5-tetrahydro-7-methoxy-8-trifluoromethyl)-2-benzoxepin-1-yl)methoxy]ethyl 4-bromobenzenesulfonate
10. 2-[(1,3,4,5-tetrahydro-7,8-methylenedioxy-2-benzoxepin-1-yl)methoxy]ethyl 4-nitrobenzenesulfonate
11. 2-[(1,3,4,5-tetrahydro-7-methoxy-5-methyl-2-benzoxepin-1-yl)methoxy]ethyl 2-methylbenzenesulfonate
12. 2-[(1,3,4,5-tetrahydro-7,9-dimethoxy-4,5-dimethoxy-2-benzoxepin-1-yl)methoxy]ethyl 4-nitrobenzenesulfonate
13. 2-[(1,3,4,5-tetrahydro-7,8,9-trimethoxy-4-methyl-2-benzoxepin-1-yl)methoxy]ethyl 4-nitrobenzenesulfonate
14. 2-[(1,3,4,5-tetrahydro-9-methoxy-4-phenyl-2-benzoxepin-1-yl)methoxy]ethyl 3-trifluoromethylbenzenesulfonate
15. 2-[(1,3,4,5-tetrahydro-7-hydroxy-5-bromo-2-benzoxepin-1-yl)methoxy]ethyl 4-nitrobenzenesulfonate
16. 2-[(1,3,4,5-tetrahydro-7,8-dimethoxy-5,5-dimethyl-2-benzoxepin-1-yl)methoxy]ethyl 4-nitrobenzenesulfonate 17. 2-[(1,3,4,5-tetrahydro-7,8-dimethoxy-4,4-dimethyl-2-benzoxepin-1-yl)methoxy]ethyl 3-trifluoromethylbenzenesulfonate
18. 2-[[1,5-dihydro-7,8-dimethoxyspiro[2-benzoxepin-4(3H)-1'-cyclopentane]-1-yl]methoxy]ethyl 4-nitrobenzenesulfonate
19. 2-[(8,9-dipropoxy-2,3,3a,4,6,10b-hexahydro-1H-benzo[c]cyclopent[e]oxepin-6-yl)methoxy]ethyl 2-ethylbenzenesulfonate
20. 2-[(1,3,4,5-tetrahydro-4-cyclopentyl-8,9-dimethoxy-2-benzoxepin-1-yl]methoxy]ethyl 4-nitrobenzenesulfonate
21. 2-[(1,3,4,5-tetrahydro-7,8-dihydroxy-5-n-propyl-2-benzoxepin-1-yl)methoxy]ethyl 4-nitrobenzenesulfonate
22. 2-[(1,3,4,5-tetrahydro-7,8-dimethoxy-9-trifluoromethyl-2-benzoxepin-1-yl)methoxy]ethyl 3-nitrobenzenesulfonate Similarly, from the appropriate 2-[(1,3,4,5-tetrahydro-2-benzoxepin-1-yl)ethoxy] or propoxy]ethanol and the appropriately substituted benzenesulfonyl chloride, the corresponding 2-[(1,3,4,5-tetrahydro-2-benzoxepin-1-yl)ethoxy]ethyl benzenesulfonates can be prepared using the procedure of Example 3.

EXAMPLE 4

2-[(1,3,4,5-tetrahydro-7,8-dimethoxy-2-benzothiepin-1-yl)methoxy]ethyl-4-nitrobenzenesulfonate To a mixture of 2-[(1,3,4,5-tetrahydro-7,8-dimethoxy-2-benzothiepin-1-yl)methoxy]ethanol and triethylamine is added p-nitribenzenesulfonyl chloride. The reaction mixture is stirred at room temperature for 30 minutes. The reaction mixture is then extracted with aqueous sodium bicarbonate and brine. The organic layer is filtered through sodium sulfate and taken to dryness. The residue is chromatographed on silica gel to give 2-[(1,3,4,5-tetrahydro-7,8-dimethoxy-2-benzothiepin-1-yl)methoxy]ethyl 4-nitrobenzenesulfonate.

Utilizing the procedure of Example 4 but substituting the appropriate 2-[(1,3,4,5-tetrahydro-2-benzothiepin-1-yl)methoxy]ethanol, the 2-[(1,3,4,5-tetrahydro-2-benzothiepin-1-yl)methoxy]ethyl benzenesulfonates of Table 9 can be prepared.

TABLE 9

1. 2-[(1,3,4,5-tetrahydro-9-methoxy-7-propyl-2-benzothiepin-1-yl)methoxy]ethyl 4-nitrobenzenesulfonate
2. 2-[(1,3,4,5-tetrahydro-9-methoxy-2-benzothiepin-1-yl)methoxy]ethyl 4-nitrobenzenesulfonate
3. 2-[(1,3,4,5-tetrahydro-6,7-dimethoxy-2-benzothiepin-1-yl)methoxy]ethyl 4-methoxybenzenesulfonate
4. 2-[(1,3,4,5-tetrahydro-7-ethoxy-2-benzothiepin-1-yl)methoxy]ethyl 4-ethylbenzenesulfonate
5. 2-[(1,3,4,5-tetrahydro-7,8,9-trimethoxy-2-benzothiepin-1-yl)methoxy]ethyl 4-nitrobenzenesulfonate
6. 2-[(1,3,4,5-tetrahydro-7-hydroxy-6-methoxy-2-benzothiepin-1-yl)methoxy]ethyl 4-chlorobenzenesulfonate
7. 2-[(1,3,4,5-tetrahydro-8-bromo-7-methoxy-2-benzothiepin-1-yl)methoxy]ethyl 4-nitrobenzenesulfonate
8. 2-[(1,3,4,5-tetrahydro-7-methoxy-8,9-dichloro-2-benzothiepin-1-yl)methoxy]ethyl 4-nitrobenzenesulfonate
9. 2-[(1,3,4,5-tetrahydro-7-methoxy-8-trifluoromethyl)-2-benzothiepin-1-yl)methoxy]ethyl 4-bromobenzenesulfonate
10. 2-[(1,3,4,5-tetrahydro-7,8-methylenedioxy-2-benzothiepin-1-yl)methoxy]ethyl 4-nitrobenzenesulfonate
11. 2-[(1,3,4,5-tetrahydro-7-methoxy-5-methyl-2-benzothiepin-1-yl)methoxy]ethyl 2-methylbenzenesulfonate
12. 2-[(1,3,4,5-tetrahydro-7,9-dimethoxy-4,5-dimethoxy-2-benzothiepin-1-yl)methoxy]ethyl 4-nitrobenzenesulfonate
13. 2-[(1,3,4,5-tetrahydro-7,8,9-trimethoxy-4-methyl-2-benzothiepin-1-yl)methoxy]ethyl 4-nitrobenzenesulfonate
14. 2-[(1,3,4,5-tetrahydro-9-methoxy-4-phenyl-2-benzothiepin-1-yl)methoxy]ethyl 3-trifluoromethylbenzenesulfonate
15. 2-[(1,3,4,5-tetrahydro-7-hydroxy-5-bromo-2-benzothiepin-1-yl)methoxy]ethyl 4-nitrobenzenesulfonate
16. 2-[(1,3,4,5-tetrahydro-7,8-dimethoxy-5,5-dimethyl-2-benzothiepin-1-yl)methoxy]ethyl 4-nitrobenzenesulfonate
17. 2-[(1,3,4,5-tetrahydro-7,8-dimethoxy-4,4-dimethyl-2-benzothiepin-1-yl)methoxy]ethyl 3-trifluoromethylbenzenesulfonate
18. 2-[[1,5-dihydro-7,8-dimethoxyspiro[2-benzothiepin-4(3H)-1'-cyclopentane]-1-yl]methoxy]ethyl 4-nitrobenzenesulfonate
19. 2-[(8,9-dipropoxy-2,3,3a,4,6,10b-hexahydro-1H-benzo[c]cyclopent[e]thiepin-6-yl)methoxy] ethyl 2-ethylbenzenesulfonate
20. 2-[(1,3,4,5-tetrahydro-4cyclopentyl-8,9-dimethoxy-2-benzothiepin-1-yl)methoxy]ethyl 4-nitrobenzenesulfonate
21. 2-[(1,3,4,5-tetrahydro-7,8-dihydroxy-5-n-propyl-2-benzothiepin-1-yl)methoxy]ethyl-4-nitrobenzenesulfonate
22. 2-[(1,3,4,5-tetrahydro-7,8-dimethoxy-9-trifluoromethyl-2-benzothiepin-1-yl)methoxy]ethyl 3-nitrobenzenesulfonate.

Similarly, following the procedure of Example 4, from the corresponding 2-[(1,3,4,5-tetrahydro-2-benzothiepin-1-yl)ethoxy] or propoxy]ethanols, the corresponding benzenesulfonates can be prepared.

EXAMPLE 5

2-[(1-methyl-7,8-dimethoxyisochroman-1-yl)methoxy]ethanol and derivatives.

Ethyl pyruvate (1.00 g, 0.0086 m), 3,4-dimethoxyphenylethanol (1.57 g, 0.0086 m), and 1 ml of BF$_3$ etherate are stirred at 25° C. in 20 ml of nitromethane for 45 minutes. The mixture is dissolved in methylene chloride and extracted with aqueous sodium bicarbonate. The organic phase is dried (sodium sulfate), concentrated, and chromatographed on silica gel to give 1.4 g of 6,7-dimethoxy-1-methyl-1-carboethoxyisochroman. A 0.5 g sample of this is dissolved in ether and treated with 100 mg of lithium aluminum hydride. After 10 minutes, the mixture is quenched with ethyl acetate and partitioned between 1 N aqueous sodium hydroxide and CH$_2$Cl$_2$. The organic phase yields 0.34 g of 6,7-dimethoxy-1-methyl-1-hydroxymethylisochroman. This is dissolved in THF and treated sequentially with sodium hydride and then the O-tetrahydropyranyl ether of chloroethanol. The adduct, upon treatment with acid and water, yields 2-[(7,8-dimethoxy-1-methyl-isochroman-1-yl)methoxy]ethanol. In the manner of Example 3, this can be converted to its benzenesulfonates

Furthermore, 2-[(1-methylisiochroman-1-yl)methoxy]ethanols, with various substituents on the isochroman ring, can be prepared by using the appropriate phenyl ethanols whose subtituents, $R_1$-$R_5$ (vide supra), are analogous to those substituents of the isochromans of Table 3.

From these compounds, the corresponding substituted benzenesulfonates can be prepared.

Furthermore, by reacting appropriate phenyl ethanols with various substituted 2-keto esters, the $R_8$ substituents of the isochroman ring (vide supra) can be varied and the disclosed $R_8$ substituents can thus be incorporated in the ring system.

Furthermore, various 1-hydroxymethylisochromans can be first treated with the O-tetrahydropyran ether of chloroethoxyethanol and then with acid and water to yield the corresponding 2-[2-((isochroman-1-yl)methoxy)ethoxy]ethanol.

EXAMPLE 6

2-[(7,8-dimethoxy-3,4-dihydro-1H-2-benzothiopyran-1-yl)methoxy]ethanol.

Ethyl pyruvate, 3,4-dimethoxyphenylethanethiol, and $BF_3$ etherate are stirred in nitromethane. The mixture is partitioned with methylene chloride and aqueous sodium bicarbonate. The organic phase is dried over sodium sulfate, concentrated, and chromatographed. The resultant benzothiopyran is dissolved in ether and treated with lithium aluminum hydride. The mixture is partitioned between aqueous sodium hydroxide and methylene chloride. The organic phase yields the corresponding alcohol. This can be dissolved in THF and treated sequentially with sodium hydroxide and then O-tetrahydropyranyl ether of chloroethanol. The adduct upon treatment with acid and water, yields 2-[(7,8-dimethoxy-3,4-dihydro-1H-2-benzothiopyran-1-yl)methoxy]ethanol. In the manner of Example 4, this can be converted to its p-nitrobenzenesulfonate.

Furthermore, 2-[(3,4-dihydro-1H-2-benzothiopyran-1-yl)methoxy]ethanols with various substituents on the thiopyran ring can be prepared by initially using the appropriate phenyl ethanethiols whose substituents, $R_1$-$R_5$ (vide supra), are analogous to those substituents of the thiopyrans of Table 2A and which are used to prepare the thiopyrans of Table 2A. These 1-methoxyethanols can then be converted to the benzenesulfonates corresponding to the benzenesulfonates of Table 8 following the procedure of Example 4 and using the appropriate benzenesulfonyl chlorides.

EXAMPLES 7 THROUGH 15

Benzoxepins and benzothiepins

A 1-alkoxyalkylbenzoxepin or benzothiepin benzenesulfonates prepared as in Examples 3 and 4 is stirred in tetrahydrofuran with 1.0 to 2.0 equivalents of $HNR_9R_{10}$. An excess of triethylamine is added. After the reaction is complete, the mixture is partitioned between aqueous potassium carbonate or sodium bicarbonate and methylene chloride. The organic phase is dried over sodium sulfate and concentrated. The residue is chromatographed on silica gel. The product is either crystallized or converted to its salt. The salt is formed by treating a solution of the compound with an appropriate acid in a suitable solvent.

EXAMPLE 7

1-[2-[(1,3,4,5-tetrahyro-7,8-dimethoxy-2-benzoxepin-1-yl)methoxy]ethyl]-4-(2-methoxyphenyl)piperazine.

A mixture of 0.50 g (1.07 mmoles) of 2-[(1,3,4,5-tetrahydro-7,8-dimethoxy-2-benzoxepin-1-yl)methoxy]ethyl]-4-nitrobenzenesulfonate, 0.22 g (1.07 mmoles) of o-methoxyphenylpiperazine, 0.15 ml (1.07 mmoles) of triethylamine, and 20 ml of tetrahydrofuran is stirred at room temperature for 24 hours. After removing the tetrahydrofuran in vacuo, the reaction mixture is extracted with methylene chloride and aqueous sodium bicarbonate. The organic layer is filtered through sodium sulfate, taken to dryness, and chromatographed on silica gel using 3% methanol:methylene chloride eluent to give 0.40 g (82%) of 1-[2-[(1,3,4,5-tetrahydro-7,8-dimethoxy-2-benzoxepin-1-yl)methoxy]ethyl]-4-(2-methoxyphenyl)piperazine. The dihydrochloride salt was prepared with hydrogen chloride in ethyl ether, m.p. 172°-175°.

Analysis:

Calc'd. for $C_{26}H_{36}N_2O_5 \cdot 2HCl \cdot H_2O$ C, 57.03; H, 7.36; N, 5.12; Cl, 12.95. Found: C, 56.94; H, 7.29; N, 5.48; Cl, 12.98.

EXAMPLE 8

1-[2-[(1,3,4,5-tetrahydro-7,8-dimethoxy-2-benzoxepin-1-yl)methoxy]ethyl]-4-hydroxy-4-(3-trifluoromethylphenyl)piperidine A mixture of 0.10 g (1.50 mmoles) of 2-[(1,3,4,5-tetrahydro-7,8-dimethoxy-2-benzoxepine-1-yl)methoxy]ethyl 4-nitrobenzenesulfonate, 0.37 g (1.50 mmoles) of 4-hydroxy-4-(3-trifluoromethylphenyl)piperidine, 0.21 ml (1.50 mmoles) of triethylamine and 30 ml of tetrahydrofuran is stirred at room temperature for 3 days, at 50° for 1 day, and again at room temperature for 2 days, after which the tetrahydrofuran is removed in vacuo. The reaction mixture is extracted with methylene chloride and aqueous sodium bicarbonate. The organic layer is filtered through sodium sulfate and taken to dryness and chromatographed on silica gel with 2% methanol:0.5% ammonium hydroxide:methylene chloride as eluent to give 0.46 g (60%) of the titled product. The hydrochloride salt is prepared with hydrogen chloride/ethyl ether; m.p. 156°-159°.

Analysis:

Calc'd. for $C_{27}H_{34}F_3NO_5 \cdot HCl \cdot 1/2H_2O$ C, 58.43; H, 6.54; N, 2.52; Cl, 6.34. Found: C, 58.60; H, 6.49; N, 2.85; Cl, 7.08.

EXAMPLE 9

1-[2-[(1,3,4,5-tetrahydro-7,8-dimethoxy-2-benzoxepin-1-yl)methoxy]ethyl]-4-(4-fluorophenyl)-piperazine A mixture of 400 mg of 2-[(1,3,4,5-tetrahydro-7,8-dimethoxy-2-benzoxepin-1-yl)methoxy]ethyl 4-nitrobenzenesulfonate, 150 mg of 4-fluorophenylpiperazine, 0.12 ml of triethylamine and tetrahydrofuran as solvent is stirred at room temperature for 18 hours after which the tetrahydrofuran is removed in vacuo. The reaction mixture is extracted with methylene chloride and aqueous sodium bicarbonate. The organic layer is filtered through sodium sulfate and taken to dryness. The residue is purified by chromatography. The product is crystallized from methylene chloride and SSB, and ether, m.p. 114°–114.5°.

EXAMPLE 10

1-[2-[(1,3,4,5-tetrahydro-7,8-dimethoxy-2-benzoxepin-1-yl)methoxy]ethyl]-4-(4-fluorophenyl)piperazine A mixture of 1.27 g (4.42 mmoles) of 2-[(1,3,4,5-tetrahydro-7,8-dimethoxy-2-benzoxepin-1-yl)methoxy]ethyl chloride, and 1.52 g (8.44 mmoles) of 1-fluorophenyl piperazine is stirred for 60 hours at 90°, neat. The product is isolated and crystallized as in Example 15.

EXAMPLE 11

1-[2-[(1,3,4,5-tetrahydro-7,8-dimethoxy-2-benzoxepin-1-yl)methoxy]ethyl]-4-(2-pyridyl)piperazine A mixture of 1.00 g (3.32 mmoles) of 2-[(1,3,4,5-tetrahydro-7,8-dimethoxy-2-benzoxepin-1-yl)methoxy]ethyl chloride and 1.14 g (6.65 mmoles) of 95% 2-pyridylpiperazine is stirred at 90° for 20 hours. Approximately 3 ml of toluene is then added and the reaction mixture is heated for an additional 28 hours. After cooling, the reaction mixture is filtered, washing with toluene, and the filtrate is extracted with (1) aqueous sodium bicarbonate and (2) brine. The organic layer is taken to dryness and the residue is chromatographed on silica gel using 3% methanol:0.5% ammonium hydroxide in methylene chloride as eluent to give 1.30 g (92%) of the stated product. The hydrochloric acid salt (dihydrate) was prepared from hydrogen chloride in ethanol.

Analysis:
Calc'd. for $C_{24}H_{33}N_3O_4 \cdot HCl \cdot 2H_2O$ C, 57.65; H, 7.46; N, 8.40. Found: C, 57.31; H, 7.69; N, 8.23.

EXAMPLE 12

1-[2-[(1,3,4,5-tetrahydro-7,8-dimethoxy-2-benzoxepin-1-yl)methoxy]ethyl]piperidine A mixture of 0.75 g of 1-(2-chloroethoxymethyl)-1,3,4,5-tetrahydro-7,8-dimethoxy-2-benzoxepine, 5 ml of piperidine, and 2 ml of toluene is stirred at 75° for six days. The reaction mixture is then extracted with methylene chloride and aqueous sodium bicarbonate. The organic layer is filtered through anhydrous sodium sulfate and taken to dryness. The crude product is chromatographed on silica gel using 3% methanol in methylene chloride to give the product. A crystalline hydrochloride salt of the titled product (m.p. 124.0°) is prepared from hydrogen chloride in ether.

EXAMPLE 13

1-[2-{(1-methyl-6,7-dimethoxy-3,4-dihydro-1H-2-benzothiopyran-1-ml)methoxy}ethyl]piperidine.

A mixture of 2-[[1-methyl-6,7-dimethoxy-3,4-dihydro-1H-2-benzothiopyran-1-yl]methoxy]ethanol 4-nitrobenzenesulfonate and piperidine is stirred at room temperature in THF. The mixture is then partitioned between methylene chloride and aqueous sodium carbonate. The title compound is isolated by chromatography and is crystallized.

EXAMPLE 14

Following the procedure used in Example 7 through 12 but substituting the appropriate 1-[2-[(1,3,4,5-tetrahydro-2-benzoxepin-1-yl)alkoxy]ethyl halides or benzene sulfonates and the appropriate amines, or starting with the appropriate benzoxepine compounds of Formula 1 and first following the general procedures described above for extending the oxyalkylene chain from q is 1 to q is 2 or 3 and then following the amination procedures used in Examples 7 to 12, the following compounds can be made.

TABLE 10

| $R_1'$ | $R_1''$ | $R_1'''$ | $R_1''''$ | $R_2$ | $R_3$ | $R_4$ | $R_5$ | $R_6$ | $R_7$ | $R_8$ | m | q | $NR_{21}R_{22}$ |
|---|---|---|---|---|---|---|---|---|---|---|---|---|---|
| H | H | propyl | —OCH₃ | H | H | H | H | H | H | H | 1 | 1 | NH(CH₂)₂-(2,3-dichlorophenyl) |
| H | H | H | —OCH₃ | H | H | H | H | H | H | H | 1 | 2 | 4-(4-chlorophenyl)piperazin-1-yl |
| OCH₃ | OCH₃ | H | H | H | H | H | H | H | H | H | 1 | 3 | (5,6-dimethylisoindolin-2-yl) |
| H | OC₂H₅ | H | H | H | H | H | H | H | H | H | 2 | 1 | 4-acetylpiperazin-1-yl |

TABLE 10-continued
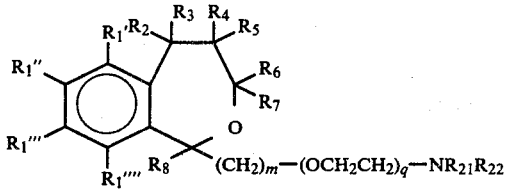
| R$_1$' | R$_1$" | R$_1$''' | R$_1$'''' | R$_2$ | R$_3$ | R$_4$ | R$_5$ | R$_6$ | R$_7$ | R$_8$ | m | q | NR$_{21}$R$_{22}$ |
|---|---|---|---|---|---|---|---|---|---|---|---|---|---|
| H | OCH$_3$ | OCH$_3$ | OCH$_3$ | H | H | H | H | H | H | H | 2 | 2 | 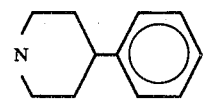 |
| —OCH$_3$ | —OH | H | H | H | H | H | H | H | H | H | 2 | 3 | 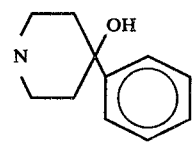 |
| H | —OCH$_3$ | Br | H | H | H | H | H | H | H | H | 3 | 1 | 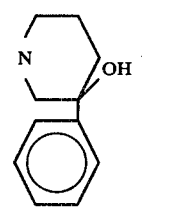 |
| H | —OCH$_3$ | Cl | Cl | H | H | H | H | H | H | H | 3 | 2 | 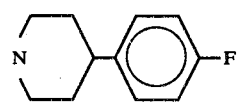 |
| H | —OCH$_3$ | —CF$_3$ | H | H | H | H | H | H | H | H | 3 | 3 | 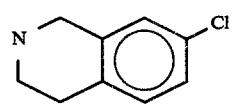 |
| H | —OCH$_2$O— | | H | H | H | H | H | H | H | H | 1 | 1 |  |
| H | —OCH$_3$ | H | H | CH$_3$ | H | H | H | H | H | H | 2 | 1 | 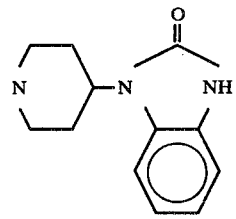 |
| H | OCH$_3$ | H | OCH$_3$ | CH$_3$ | H | CH$_3$ | H | H | H | H | 3 | 2 | 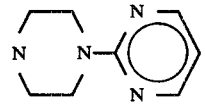 |
| H | OCH$_3$ | OCH$_3$ | OCH$_3$ | H | H | OCH$_3$ | CH$_3$ | H | H | H | 2 | 3 | 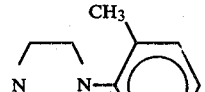 |
| H | H | H | OCH$_3$ | H | H | H | C$_6$H$_5$ | H | H | H | 1 | 3 | 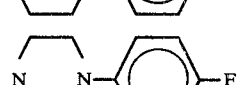 |
| H | OH | H | H | H | Br | H | H | H | H | H | 1 | 1 |  |

TABLE 10-continued

Structure: benzene ring with substituents $R_1'$, $R_1''$, $R_1'''$, $R_1''''$, $R_1'''''$, and side chain with $R_2, R_3, R_4, R_5, R_6, R_7$ and $R_8$—O—$(CH_2)_m$—$(OCH_2CH_2)_q$—$NR_{21}R_{22}$

| $R_1'$ | $R_1''$ | $R_1'''$ | $R_1''''$ | $R_2$ | $R_3$ | $R_4$ | $R_5$ | $R_6$ | $R_7$ | $R_8$ | m | q | $NR_{21}R_{22}$ |
|---|---|---|---|---|---|---|---|---|---|---|---|---|---|
| H | OCH₃ | OCH₃ | H | CH₃ | CH₃ | H | H | H | H | H | 2 | 2 | —NH(CH₂)₂—(3,4-dichlorophenyl) |
| H | OCH₃ | OCH₃ | H | H | H | CH₃ | CH₃ | H | H | H | 3 | 3 | piperazinyl-(3-bromophenyl) |
| H | OCH₃ | OCH₃ | H | (cyclopentyl) | | H | H | H | H | H | 3 | 1 | 6,7-dimethyl-1,2,3,4-tetrahydroisoquinolin-2-yl |
| H | OC₃H₇ | OC₃H₇ | H | H* | H | * | H | H | H | H | 1 | 1 | piperazinyl-(4-ethylphenyl) |
| H | H | OCH₃ | OCH₃ | H | H | (cyclopentyl) | H | H | H | H | 1 | 1 | 6-hydroxy-1,2,3,4-tetrahydroisoquinolin-2-yl |
| H | OH | OH | H | C₃H₇ | H | H | H | H | H | H | 1 | 1 | —NH(CH₂)₂—(3,4-dimethoxyphenyl) |
| H | —OCH₃ | —OCH₃ | H | H | H | H | H | H | H | CH₃ | 1 | 3 | —N(CH₃)₂ |
| H | —OCH₃ | —OCH₃ | H | H | H | H | H | H | H | CH₃ | 1 | 3 | morpholino (N O) |
| H | —OCH₃ | —OCH₃ | H | CH₃ | CH₃ | H | H | H | H | CH₃ | 1 | 3 | —N—H butyl |
| H | OCH₃ | —OCH₃ | H | H | H | CH₃ | CH₃ | H | H | CH₃ | 2 | 3 | piperazinyl-(4-fluorophenyl) |
| H | OCH₃ | OCH₃ | H | CH₃ | CH₃ | H | H | H | H | C₆H₅ | 1 | 3 | —NH-t-butyl |
| H | OCH₃ | OCH₃ | H | H | H | H | H | H | H | C₆H₅ | 1 | 3 | —NH₂ |

* $R_2 + R_4 =$ (cyclopentyl ring)

EXAMPLE 15

Following procedures similar to those of Examples 7 through 12 and 14 but substituting the appropriate (1,3,4,5-tetrahydro-2-benzothiepin-1-yl)alkoxyethyl halides or benzenesulfonates for the corresponding benzoxepins, or the appropriate Formula I compounds (with W=S and b=1), the 2-benzothiepins of Table 11 can be prepared.

TABLE 11

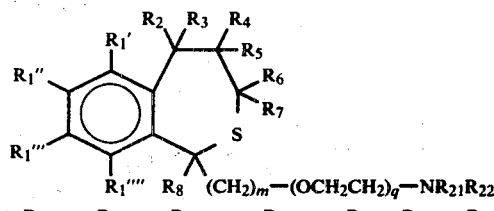

| $R_1'$ | $R_1''$ | $R_1'''$ | $R_1''''$ | $R_2$ | $R_3$ | $R_4$ | $R_5$ | $R_6$ | $R_7$ | $R_8$ | m | q | $NR_{21}R_{22}$ |
|---|---|---|---|---|---|---|---|---|---|---|---|---|---|
| H | H | propyl | -OCH$_3$ | H | H | H | H | H | H | H | 1 | 1 | NH(CH$_2$)$_2$-(3,4-diClC$_6$H$_3$) |
| H | H | H | -OCH$_3$ | H | H | H | H | H | H | H | 1 | 2 | 4-(4-chlorophenyl)piperazin-1-yl |
| OCH$_3$ | OCH$_3$ | H | H | H | H | H | H | H | H | H | 1 | 3 | 6,7-dimethyl-1,2,3,4-tetrahydroisoquinolin-2-yl |
| H | OC$_2$H$_5$ | H | H | H | H | H | H | H | H | H | 2 | 1 | 4-acetylpiperazin-1-yl |
| H | OCH$_3$ | OCH$_3$ | OCH$_3$ | H | H | H | H | H | H | H | 2 | 2 | 4-phenylpiperidin-1-yl |
| -OCH$_3$ | -OH | H | H | H | H | H | H | H | H | H | 2 | 3 | 4-hydroxy-4-phenylpiperidin-1-yl |
| H | -OCH$_3$ | Br | H | H | H | H | H | H | H | H | 3 | 1 | 3-hydroxy-3-phenylpiperidin-1-yl |
| H | -OCH$_3$ | Cl | Cl | H | H | H | H | H | H | H | 3 | 2 | 4-(4-fluorophenyl)piperidin-1-yl |
| H | -OCH$_3$ | -CF$_3$ | H | H | H | H | H | H | H | H | 3 | 3 | 7-chloro-1,2,3,4-tetrahydroisoquinolin-2-yl |
| H | -OCH$_2$O- | | H | H | H | H | H | H | H | 1 | 1 | 4-(2-oxo-2,3-dihydrobenzimidazol-1-yl)piperidin-1-yl |
| H | -OCH$_3$ | H | H | CH$_3$ | H | H | H | H | H | H | 2 | 1 | 4-(pyrimidin-2-yl)piperazin-1-yl |
| H | OCH$_3$ | H | OCH$_3$ | CH$_3$ | H | CH$_3$ | H | H | H | H | 3 | 2 | 4-(2-methylphenyl)piperazin-1-yl |
| H | OCH$_3$ | OCH$_3$ | OCH$_3$ | H | H | OCH$_3$ | CH$_3$ | H | H | H | 2 | 3 | 4-(4-fluorophenyl)piperazin-1-yl |

TABLE 11-continued

| $R_1'$ | $R_1''$ | $R_1'''$ | $R_1''''$ | $R_2$ | $R_3$ | $R_4$ | $R_5$ | $R_6$ | $R_7$ | $R_8$ | m | q | $NR_{21}R_{22}$ |
|---|---|---|---|---|---|---|---|---|---|---|---|---|---|
| H | H | H | OCH₃ | H | H | H | phenyl | H | H | H | 1 | 3 | N-piperazinyl-(2-methoxyphenyl) |
| H | OH | H | H | H | Br | H | H | H | H | H | 1 | 1 | 6,7-dimethoxy-1,2,3,4-tetrahydroisoquinolin-2-yl |
| H | OCH₃ | OCH₃ | H | CH₃ | CH₃ | H | H | H | H | H | 2 | 2 | NH(CH₂)₂-(3,4-dichlorophenyl) |
| H | OCH₃ | OCH₃ | H | H | H | CH₃ | CJ₃ | H | H | H | 3 | 3 | N-piperazinyl-(3-bromophenyl) |
| H | OCH₃ | OCH₃ | H | cyclopentyl | | | H | H | H. | H | 3 | 1 | 6,7-dimethyl-1,2,3,4-tetrahydroisoquinolin-2-yl |
| H | OC₃H₇ | OC₃H₇ | H | * | H | * | H | H | H | H | 1 | 1 | N-piperazinyl-(4-ethylphenyl) |
| H | H | OCH₃ | OCH₃ | H | H | cyclopentyl | | H | H | H | 1 | 1 | 7-hydroxy-1,2,3,4-tetrahydroisoquinolin-2-yl |
| H | OH | OH | H | C₃H₇ | H | H | H | H | H | H | 1 | 1 | NH(CH₂)₂-(3,4-dimethoxyphenyl) |
| H | -OCH₃ | -OCH₃ | H | H | H | H | H | H | H | CH₃ | 1 | 3 | —N(CH₃)₂ |
| H | -OCH₃ | -OCH₃ | H | H | H | H | H | H | H | CH₃ | 1 | 3 | morpholino |
| H | -OCH₃ | -OCH₃ | H | CH₃ | CH₃ | H | H | H | H | CH₃ | 1 | 3 | —N—H butyl |
| H | OCH₃ | -OCH₃ | H | H | H | CH₃ | CH₃ | H | H | CH₃ | 2 | 3 | N-piperazinyl-(4-fluorophenyl) |
| H | OCH₃ | OCH₃ | H | CH₃ | CH₃ | H | H | H | H | C₆H₅ | 1 | 3 | —NH-t-butyl |
| H | OCH₃ | OCH₃ | H | H | H | H | H | H | H | C₆H₅ | 1 | 3 | —NH₂ |

*R₂ + R₄ = cyclopentyl

EXAMPLE 16

Following the procedures described in Examples 7 through 12, but substituting either the appropriate [isochroman-1-yl]alkoxyethyl halides, or [isochroman-1-yl]alkoxyethyl benzenesulfonates, or starting with the appropriate isochromans of Formula I and first following the general procedures described above for extending the oxyalkylene chain from q is 1 to q is 2 or 3 and then following the amination procedures used in Examples 7 through 12, the compounds of Table 12 can be made.

TABLE 12

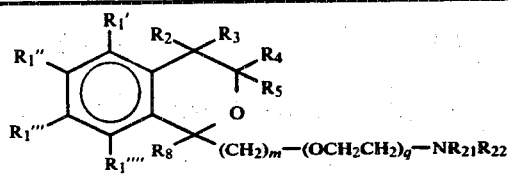

| R₁' | R₁'' | R₁''' | R₁'''' | R₂ | R₃ | R₄ | R₅ | R₈ | m | q | NR₂₁R₂₂ |
|---|---|---|---|---|---|---|---|---|---|---|---|
| H | H | propyl | —OCH₃ | H | H | H | H | H | 1 | 1 | NH(CH₂)₂-(3,4-diClC₆H₃) |
| H | H | H | —OCH₃ | H | H | H | H | H | 1 | 2 | piperazinyl-(4-ClC₆H₄) |
| OCH₃ | OCH₃ | H | H | H | H | H | H | H | 1 | 3 | 6,7-dimethyl-tetrahydroisoquinolinyl |
| H | OC₂H₅ | H | H | H | H | H | H | H | 2 | 1 | 4-acetylpiperazinyl |
| H | OCH₃ | OCH₃ | OCH₃ | H | H | H | H | H | 2 | 2 | 4-benzylidenepiperidinyl |
| —OCH₃ | —OH | H | H | H | H | H | H | H | 2 | 3 | 4-hydroxy-4-phenylpiperidinyl |
| H | —OCH₃ | Br | H | H | H | H | H | H | 3 | 1 | 4-hydroxy-4-phenylpiperidinyl |
| H | —OCH₃ | Cl | Cl | H | H | H | H | H | 3 | 2 | 4-(4-fluorophenyl)piperidinyl |
| H | —OCH₃ | —CF₃ | H | H | H | H | H | H | 3 | 3 | 7-chloro-tetrahydroisoquinolinyl |
| H | —O—CH₂—O— | | H | H | H | H | H | H | 1 | 1 | 4-(3-phenylureido)piperidinyl |
| H | —OCH₃ | H | H | CH₃ | H | H | H | H | 2 | 1 | 4-(2-pyridyl)piperazinyl |
| H | OCH₃ | H | OCH₃ | CH₃ | H | CH₃ | H | H | 3 | 2 | 4-(2-methylphenyl)piperazinyl |
| H | OCH₃ | OCH₃ | OCH₃ | OCH₃ | H | OCH₃ | H | H | 2 | 3 | 4-(4-fluorophenyl)piperazinyl |

TABLE 12-continued

Structure:
R₁″—, R₁′—, R₂, R₃, R₄, R₅ on a phenyl ring with side chain —C(R₈)(CH₂)ₘ—(OCH₂CH₂)_q—NR₂₁R₂₂, with O linkage

| R₁′ | R₁″ | R₁‴ | R₁″″ | R₂ | R₃ | R₄ | R₅ | R₈ | m | q | NR₂₁R₂₂ |
|---|---|---|---|---|---|---|---|---|---|---|---|
| H | H | H | OCH₃ | H | H | H | C₆H₅ (phenyl) | H | 1 | 3 | piperazinyl-(2-OCH₃-phenyl) |
| H | OH | H | H | H | H | F | H | H | 1 | 1 | 6,7-dimethoxy-1,2,3,4-tetrahydroisoquinolin-2-yl |
| H | OCH₃ | OCH₃ | H | CH₃ | CH₃ | H | H | H | 2 | 2 | —NH(CH₂)₂—(3,4-dichlorophenyl) |
| H | OCH₃ | OCH₃ | H | H | H | CH₃ | CH₃ | H | 3 | 3 | piperazinyl-(3-bromophenyl) |
| H | OCH₃ | OCH₃ | H | cyclopentyl (R₂+R₃) | | H | H | H | 3 | 1 | 6,7-dimethyl-1,2,3,4-tetrahydroisoquinolin-2-yl |
| H | OC₃H₇ | OC₃H₇ | H | H | cyclobutyl (R₃+R₄) | | H | H | 1 | 1 | piperazinyl-(4-ethylphenyl) |
| H | H | OCH₃ | OCH₃ | H | H | cyclopentyl (R₄+R₅) | | H | 1 | 1 | 6-hydroxy-1,2,3,4-tetrahydroisoquinolin-2-yl |
| H | OH | OH | H | H | H | C₃H₇ | H | H | 1 | 1 | —NH(CH₂)₂—(3,4-dimethoxyphenyl) |
| H | —OCH₃ | —OCH₃ | H | H | H | CH₃ | H | CH₃ | 1 | 3 | —N(CH₃)₂ |
| H | —OCH₃ | —OCH₃ | H | C₂H₅ | H | H | H | CH₃ | 1 | 3 | morpholino |
| H | —OCH₃ | —OCH₃ | H | cyclopentyl (R₂+R₃) | | H | H | CH₃ | 1 | 3 | —N—H butyl |
| H | OCH₃ | —OCH₃ | H | cyclohexyl (R₃+R₄) | | H | H | CH₃ | 2 | 3 | piperazinyl-(4-fluorophenyl) |
| H | OCH₃ | OCH₃ | H | CH₃ | H | H | H | C₆H₅ | 1 | 3 | —NH-t-butyl |
| H | OCH₃ | OCH₃ | H | H | H | CH₃ | H | C₆H₅ | 1 | 3 | —NH₂ |

EXAMPLE 17

The compounds of Table 13 can be prepared using the procedures of Examples 7 through 13 and 16 starting from the appropriate [3,4-dihydro-1H-2-benzothiopyran-1-yl]-alkoxyethyl benzenesulfonates, or the corresonding chlorides, and the appropriate amines.

TABLE 13

(structure shown with substituents $R_1'$, $R_1''$, $R_1'''$, $R_1''''$, $R_2$, $R_3$, $R_4$, $R_5$, $R_8$, and $(CH_2)_m-(OCH_2CH_2)_q-NR_{21}R_{22}$ chain with S)

| $R_1'$ | $R_1''$ | $R_1'''$ | $R_1''''$ | $R_2$ | $R_3$ | $R_4$ | $R_5$ | $R_8$ | m | q | $NR_{21}R_{22}$ |
|---|---|---|---|---|---|---|---|---|---|---|---|
| H | H | propyl | —OCH₃ | H | H | H | H | H | 1 | 1 | —NH(CH₂)₂-(3,4-dichlorophenyl) |
| H | H | H | —OCH₃ | H | H | H | H | H | 1 | 2 | 4-(4-chlorophenyl)piperazin-1-yl |
| OCH₃ | OCH₃ | H | H | H | H | H | H | H | 1 | 3 | 6,7-dimethyl-1,2,3,4-tetrahydroisoquinolin-2-yl |
| H | OC₂H₅ | H | H | H | H | H | H | H | 2 | 1 | 4-acetylpiperazin-1-yl |
| H | OCH₃ | OCH₃ | OCH₃ | H | H | H | H | H | 2 | 2 | 4-phenylpiperidin-1-yl |
| —OCH₃ | —OH | H | H | H | H | H | H | H | 2 | 3 | 4-hydroxy-4-phenylpiperidin-1-yl |
| H | —OCH₃ | Br | H | H | H | H | H | H | 3 | 1 | 3-hydroxy-3-phenylpiperidin-1-yl |
| H | —OCH₃ | Cl | Cl | H | H | H | H | H | 3 | 2 | 4-(4-fluorophenyl)piperidin-1-yl |
| H | —OCH₃ | —CF₃ | H | H | H | H | H | H | 3 | 3 | 7-chloro-1,2,3,4-tetrahydroisoquinolin-2-yl |
| H | —OCH₂O— | | H | H | H | H | H | H | 1 | 1 | 4-(2,3-dihydro-1H-benzimidazol-1-yl)piperidin-1-yl |
| H | —OCH₃ | H | H | CH₃ | H | H | H | H | 2 | 1 | 4-(pyrimidin-2-yl)piperazin-1-yl |

TABLE 13-continued

Structure:
```
      R1'    R2  R3
  R1''         R4
              R5
  R1'''       S
      R1''''  R8  (CH2)m—(OCH2CH2)q—NR21R22
```

| R1' | R1'' | R1''' | R1'''' | R2 | R3 | R4 | R5 | R8 | m | q | NR21R22 |
|---|---|---|---|---|---|---|---|---|---|---|---|
| H | OCH3 | H | OCH3 | CH3 | H | CH3 | H | H | 3 | 2 | piperazinyl-(2-methylphenyl) |
| H | OCH3 | OCH3 | OCH3 | OCH3 | H | OCH3 | H | H | 2 | 3 | piperazinyl-(4-fluorophenyl) |
| H | H | H | OCH3 | H | H | H | phenyl | H | 1 | 3 | piperazinyl-(2-methoxycyclohexyl) |
| H | OH | H | H | H | H | F | H | H | 1 | 1 | 6,7-dimethoxy-tetrahydroisoquinolinyl |
| H | OCH3 | OCH3 | H | CH3 | CH3 | H | H | H | 2 | 2 | NH(CH2)2-(3,4-dichlorophenyl) |
| H | OCH3 | OCH3 | H | H | H | CH3 | CH3 | H | 3 | 3 | piperazinyl-(3-bromo-phenyl) |
| H | OCH3 | OCH3 | H | cyclopentyl | | H | H | H | 3 | 1 | 6,7-dimethyl-tetrahydroisoquinolinyl |
| H | OC3H7 | OC3H7 | H | H | H | cyclopropyl | H | H | 1 | 1 | piperazinyl-(4-ethylphenyl) |
| H | H | OCH3 | OCH3 | H | H | cyclopentyl | H | H | 1 | 1 | 7-hydroxy-tetrahydroisoquinolinyl |
| H | OH | OH | H | H | H | C3H7 | H | H | 1 | 1 | NH(CH2)2-(3,4-dimethoxyphenyl) |
| H | —OCH3 | —OCH3 | H | H | H | CH3 | H | CH3 | 1 | 3 | —N(CH3)2 |
| H | —OCH3 | —OCH3 | H | C2H5 | H | H | H | CH3 | 1 | 3 | morpholino |
| H | —OCH3 | —OCH3 | H | cyclopentyl | | H | H | CH3 | 1 | 3 | —N—H butyl |
| H | OCH3 | —OCH3 | H | cyclohexyl | | H | H | CH3 | 2 | 3 | piperazinyl-(4-fluorophenyl) |
| H | OCH3 | OCH3 | H | CH3 | H | H | H | C6H5 | 1 | 3 | —NH-t-butyl |

TABLE 13-continued

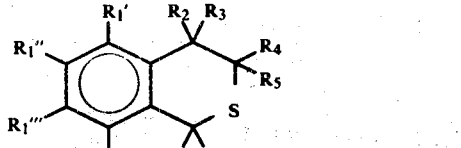

| R₁' | R₁'' | R₁''' | R₁'''' | R₂ | R₃ | R₄ | R₅ | R₈ | m | q | NR₂₁R₂₂ |
|---|---|---|---|---|---|---|---|---|---|---|---|
| H | OCH₃ | OCH₃ | H | H | H | CH₃ | H | C₆H₅ | 1 | 3 | —NH₂ |

EXAMPLE 18

A lot of 10,000 tablets, each containing 25 mg 1-[2-[(1,3,4,5-tetrahydro-7,8-dimethoxy-2-benzoxepin-1-yl)-methoxy]ethyl]-4-hydroxy-4-(3-trifluoromethyl-phenyl)piperidine as essential active ingredient is prepared from the following types and amounts of ingredients:

| | |
|---|---|
| 1-[2-[(1,3,4,5-tetrahydro-7,8-dimethoxy-2-benzoxepin-1-yl)-methoxy]ethyl]-4-hydroxy-4-(3-trifluoromethyl phenyl)-piperidine | 250 g |
| Dicalcium phosphate | 1000 g |
| Methylcellulose, U.S.P. (15 cps) | 60 g |
| Talc | 150 g |
| Corn Starch | 200 g |
| Magnesium stearate | 10 g |

The compound and dicalcium phosphate are mixed well, granulated with 7.5 percent solution of methyl cellulose in water, passed through a No. 8 screen and dried carefully. The dried granules are passed through a No. 12 screen, mixed thoroughly with the talc, starch and magnesium stearate, and compressed into tablets.

These tablets are useful in treating hypertension at a dose of two tablets per day.

EXAMPLE 19

A lot of 10,000 tablets, each containing 50 mg of 1-[2-[(1,3,4,5-tetrahydro-7,8-dimethoxy-2-benzoxepin-1-yl)-methoxy]ethyl]-4-(2-methoxyphenyl)piperazine is prepared from the following types and amounts of ingredients:

| | |
|---|---|
| 1-[2-[(1,3,4,5-tetrahydro-7,8-dimethoxy-2-benzoxepin-1-yl)-methoxy]ethyl]-4-(2-methoxyphenyl)-piperazine | 500 g |
| Dicalcium Phosphate | 1000 g |
| Methylcellulose, U.S.P. (15 cps) | 60 g |
| Talc | 150 g |
| Corn Starch | 200 g |
| Magnesium stearate | 10 g |

The compound and dicalcium phosphate are mixed well, granulated with 7.5 percent solution of methyl cellulose in water, passed through a No. 8 screen and dried carefully. The dried granules are passed through a No. 12 screen, mixed thoroughly with the talc, starch and magnesium stearate, and compressed into tablets.

These tablets are useful in treating CNS disorders, particularly psychosis, at a dose of one tablet every eight hours.

EXAMPLE 20

A sterile preparation suitable for intramuscular injection and containing 25 mg 1-[2-[(1,3,4,5-tetrahydro-7,8-dimethoxy-2-benzoxepin-1-yl)methoxy]ethyl]-4-hydroxy-4-(3-trifluoromethylphenyl)piperidine hydrochloride in each milliliter is prepared from the following types and amounts of ingredients:

| | |
|---|---|
| 1-[2-[(1,3,4,5-tetrahydro-7,8-dimethoxy-2-benzoxepin-1-yl)-methoxy]ethyl]-4-hydroxy-4-(3-trifluoromethylphenyl)piperidine hydrochloride | 25 g |
| Benzyl benzoate | 200 ml |
| Methylparaben | 1.5 g |
| Propylparaben | 0.5 g |
| Cottonseed oil q.s. to | 1000 ml |

One milliliter of this sterile preparation is injected for treatment of hypertension two times a day.

EXAMPLE 21

A sterile preparation suitable for intramuscular injection and containing 60 mg of 1-[2-[(1,3,4,5-tetrahydro-7,8-dimethoxy-2-benzoxepin-1-yl)methoxy]ethyl]-4-(2-methoxyphenyl)piperazine hydrochloride in each milliliter is prepared from the following ingredients:

| | |
|---|---|
| 1-[2-[(1,3,4,5-tetrahydro-7,8-dimethoxy-2-benzoxepin-1-yl)-methoxy]ethyl]-4-(2-methoxy-phenyl)piperazine hydrochloride | 60 g |
| Benzyl benzoate | 200 ml |
| Methylparaben | 1.5 g |
| Propylparaben | 0.5 g |
| Cottonseed oil q.s. to | 1000 ml |

One milliliter of this sterile preparation is injected for the treatment of psychosis at intervals of 8 hours.

EXAMPLE 22

One thousand two-piece hard gelatin capsules for oral use, each containing 15 mg of 1-[(2-[(1,3,4,5-tetrahydro-7,8-dimethoxy-2-benzoxepin-1-yl)methoxy]ethyl]-4-(2-methoxyphenyl)piperazine are prepared from the following ingredients:

| | | |
|---|---|---|
| 1-[2-[(1,3,4,5-tetrahydro-7,8-dimethoxy-2-benzoxepin-1-yl)-methoxy]ethyl]-4-(2-methoxyphenyl)-piperazine | 15 | g |
| Lactose, U.S.P. | 50 | g |
| Starch, U.S.P. | 15 | g |
| Talc, U.S.P. | 3.5 | g |

| -continued | |
|---|---|
| Calcium stearate | 1.5 g |

The micronized active ingredient is mixed with the starch-lactose mixture followed by the talc and calcium stearate. The final mixture is then encapsulated in the usual manner.

One capsule every 12 hours is administered to treat hypertension.

EXAMPLE 23

One thousand two-piece hard gelatin capsules for oral use, each containing 60 mg of 1-[(2[(1,3,4,5-tetrahydro-7,8-dimethoxy-2-benzoxepin-1-yl)methoxy]ethyl]-4-(2-pyridyl)piperazine are prepared from the following ingredients:

| 1-[2-[(1,3,4,5-tetrahydro-7,8-dimethoxy-2-benzoxepin-1-yl)methoxy]ethyl]-4-(2-pyridyl)-piperazine | 60 g |
|---|---|
| Lactose, U.S.P. | 50 g |
| Starch, U.S.P. | 15 g |
| Talc, U.S.P. | 3.5 g |
| Calcium stearate | 1.5 g |

The micronized active ingredient is mixed with the starch-lactose mixture followed by the talc and calcium stearate. The final mixture is then encapsulated in the usual manner. One capsule is used every 8 hours to treat CNS disorders, particularly psychosis.

EXAMPLE 24

An aqueous preparation for oral use containing in each 5 ml (1 teaspoon) 75 mg of 1-[2-[(1,3,4,5-tetrahydro-7,8-dimethoxy-2-benzoxepin-1-yl)methoxy]ethyl]-4-(2-pyridinyl)piperazine is prepared from the following ingredients:

| 1-[2-[(1,3,4,5-tetrahydro-7,8-dimethoxy-2-benzoxepin-1-yl)methoxy]-methoxy]ethyl]-4-(2-pyridinyl)-piperazine hydrochloride | 80 g |
|---|---|
| Methylparaben, U.S.P. | 0.75 g |
| Propylparaben, U.S.P. | 0.25 g |
| Saccharin sodium | 1.25 g |
| Cyclamate sodium | 0.25 g |
| Glycerin | 300 ml |
| Tragacanth powder | 1.0 g |
| Orange oil Flavor | 1.0 g |
| F.D. and C. orange dye | 0.75 g |
| Deionized water, q.s. to | 1000 ml |

A dose of one teaspoon per day is useful for treating hypertension.

EXAMPLE 25

An aqueous preparation for oral use containing in each teaspoon (5 ml) 100 mg of 1-[2-[(1,3,4,5-tetrahydro-7,8-dimethoxy-2-benzoxepin-1-yl)methoxy]ethyl]-4-(2-pyridyl)piperazine for use in treating psychotic disorders is prepared from the following ingredients:

| 1-[2-[(1,3,4,5-tetrahydro-7,8-dimethoxy-2-benzoxepin-1-yl)methoxy]ethyl]-4-(2-pyridyl)-piperazine hydrochloride | 110 g |
|---|---|
| Methylparaben, U.S.P. | 0.75 g |
| Propyl paraben, U.S.P. | 0.25 g |

| -continued | |
|---|---|
| Saccharin sodium | 1.25 g |
| Cyclamate sodium | 0.25 g |
| Glycerin | 300 ml |
| Tragacanth powder | 1.0 g |
| Orange oil flavor | 1.0 g |
| F.D. and C. orange dye | 0.75 g |
| Deionized water, q.s. to | 1000 ml |

A dose of one to two teaspoons per day is useful in treating CNS diseases, particularly psychosis.

EXAMPLE 26

Following the procedure of Example 1 but substituting the appropriate ethyl chloride from Preparation 6, the corresponding 2-[2-(7,8-dimethoxy-2-benzoxepin-1-yl)ethoxy]ethanol can be prepared.

I claim:

1. A compound of the formula:

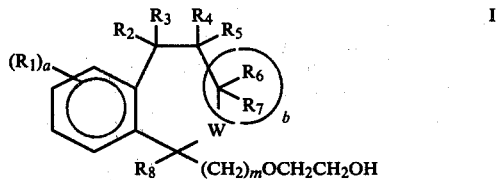

wherein $R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

b is zero or one;

$R_2$ through $R_7$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, or $R_6$ and $R_7$ are taken together with the carbon to which they are attached; cycloalkyl of four through seven carbons when $R_2$ and $R_4$ or $R_4$ and $R_6$ are taken together with the carbons to which they are attached; and cycloalkyl of five or six carbons, with the proviso that no more than one ring may be attached to any one carbon and that at least two of $R_2$ through $R_7$ are hydrogen.

$R_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;

m is one to three; and

W is oxygen or sulfur.

2. A compound according to claim 1 having the formula

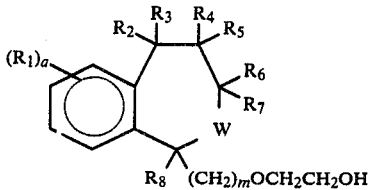

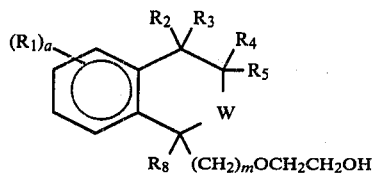

wherein
- $R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;
- a is one through three;
- $R_2$ through $R_7$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, or $R_6$ and $R_7$ are taken together with the carbon to which they are attached; cycloalkyl of four through seven carbons when $R_2$ and $R_4$ and $R_6$ are taken together with the carbons to which they are attached; and cycloalkyl of five or six carbons, with the overall provisos that no more than one ring may be attached to any one carbon and that at least two of $R_2$ through $R_7$ are hydrogen.
- $R_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;
- m is one to three; and
- W is oxygen or sulfur.

3. A compound according to claim 1 having the formula wherein
- $R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;
- a is one through three;
- $R_2$ through $R_5$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, are taken together with the carbon to which they are attached; cycloalkyl of four through seven carbons when $R_2$ and $R_4$ are taken together with the carbons to which they are attached; and cycloalkyl of five or six carbons, with the overall provisos that no more than one ring may be attached to any one carbon and that at least two of $R_2$ through $R_5$ are hydrogen.
- $R_6$ is alkyl of one through four carbons, hydrogen, or phenyl unsubstituted or substituted with a maximum of three substituents selected from the group consisting of alkyl of one through three carbons, halo, alkoxy of one through three carbons, and trihaloalkyl of one or two carbons; m is one to three; and
- W is oxygen or sulfur.

4. A compound according to claim 2 wherein $(R_1)_a$ is 7,8-dimethoxy, $R_2$ through $R_8$ is hydrogen, b is 1 and W is oxygen so that the specific embodiment is 2-[(1,3,4,5-tetrahydro-7,8-dimethoxy-2-benzoxepin-1-yl)methoxy]ethanol.

* * * * *